(12) United States Patent
Chin et al.

(10) Patent No.: US 10,912,647 B2
(45) Date of Patent: Feb. 9, 2021

(54) VASCULAR VALVE PROSTHESIS

(71) Applicant: Innovein, Inc., San Carlos, CA (US)

(72) Inventors: Albert K Chin, Palo Alto, CA (US); Andrew Moll, San Carlos, CA (US); Andrew Kwok, San Carlos, CA (US); Thomas A Kramer, San Carlos, CA (US); Austin Walker, Hillsborough, CA (US); Eric Chen, San Carlos, CA (US)

(73) Assignee: INNOVEIN, INC., San Carlos, CA (US)

( * ) Notice: Subject to any disclaimer, the term of this patent is extended or adjusted under 35 U.S.C. 154(b) by 75 days.

(21) Appl. No.: 16/007,471

(22) Filed: Jun. 13, 2018

(65) Prior Publication Data

US 2018/0289486 A1    Oct. 11, 2018

Related U.S. Application Data

(63) Continuation-in-part of application No. 15/247,523, filed on Aug. 25, 2016, now Pat. No. 10,231,838.
(Continued)

(51) Int. Cl.
*A61F 2/24* (2006.01)
*A61F 2/06* (2013.01)

(52) U.S. Cl.
CPC .............. *A61F 2/2475* (2013.01); *A61F 2/06* (2013.01); *A61F 2/2424* (2013.01);
(Continued)

(58) Field of Classification Search
CPC ................. A61F 2/2424; A61F 2/2475; A61F 2230/001; A61F 2250/0039;
(Continued)

(56) References Cited

U.S. PATENT DOCUMENTS 3,466,671 A * 9/1969 Siposs .............. A61F 2/2424
                                                          623/2.35
3,593,343 A    7/1971 Viggers
(Continued)

FOREIGN PATENT DOCUMENTS

CN    103313681 A    9/2013
CN    104427956 A    8/2015
(Continued)

OTHER PUBLICATIONS

European Search Report for Application No. 16840136.2 dated Mar. 19, 2019, 9 pages.
(Continued)

*Primary Examiner* — Brian E Pellegrino
(74) *Attorney, Agent, or Firm* — Merchant & Gould P.C.

(57) ABSTRACT

A valve prosthetic implant for treating a vein or other blood vessel includes a tubular, expandable anchoring frame extending from a proximal end to a distal end of the implant, a valve seat formed at or near the middle of the anchoring frame, an expandable ball disposed within the lumen of the anchoring frame, and a ball retention tether attached to the expandable ball and to the valve seat and/or the anchoring frame. The anchoring frame may include a cylindrical proximal portion at the proximal end, a cylindrical distal portion at the distal end, an inwardly angled inlet portion between the cylindrical proximal portion and a middle of the anchoring frame, and an inwardly angled outlet portion between the cylindrical distal portion and the middle of the anchoring frame.

26 Claims, 22 Drawing Sheets

Related U.S. Application Data

(60) Provisional application No. 62/209,351, filed on Aug. 25, 2016, provisional application No. 62/356,337, filed on Jun. 29, 2016, provisional application No. 62/518,859, filed on Jun. 13, 2017, provisional application No. 62/610,338, filed on Dec. 26, 2017.

(52) U.S. Cl.
CPC ... *A61F 2002/068* (2013.01); *A61F 2230/001* (2013.01); *A61F 2250/0003* (2013.01); *A61F 2250/0096* (2013.01)

(58) Field of Classification Search
CPC .... A61F 2220/0016; A61F 2310/00005; A61F 2210/0085; A61F 2/12; A61F 2002/4415; A61F 2/06; A61F 2/2436; A61F 2/2427; A61B 2018/00416; A61B 17/12113; A61B 17/8836
See application file for complete search history.

(56) References Cited

U.S. PATENT DOCUMENTS

| | | | |
|---|---|---|---|
| 3,890,968 A | 6/1975 | Pierce | |
| 3,911,502 A | 10/1975 | Boretos | |
| 4,030,520 A | 6/1977 | Sands | |
| 4,922,905 A | 5/1990 | Strecker | |
| 5,146,933 A * | 9/1992 | Boyd | A61F 2/12 128/899 |
| 5,332,402 A | 7/1994 | Teitelbaum | |
| 5,397,351 A | 3/1995 | Pavcnik | |
| 5,697,968 A | 12/1997 | Rogers et al. | |
| 5,810,847 A | 9/1998 | Laufer | |
| 6,293,955 B1 | 9/2001 | Houser | |
| 6,299,637 B1 | 10/2001 | Shaolian | |
| 6,315,793 B1 | 11/2001 | Bokros | |
| 6,440,164 B1 | 8/2002 | DiMatteo | |
| 7,112,220 B2 | 9/2006 | Houston | |
| 7,435,257 B2 | 10/2008 | Lashinski et al. | |
| 7,449,027 B2 | 11/2008 | Hunt | |
| 7,955,346 B2 | 6/2011 | Mauch | |
| 8,167,928 B2 | 5/2012 | Melzer | |
| 8,246,676 B2 | 8/2012 | Acosta | |
| 8,377,115 B2 | 2/2013 | Thompson | |
| 8,425,550 B2 * | 4/2013 | Elliott | A61B 17/12022 606/200 |
| 8,617,238 B2 | 12/2013 | Palmaz | |
| 8,956,405 B2 | 2/2015 | Wang | |
| 9,737,422 B2 | 8/2017 | Armstrong | |
| 10,231,838 B2 | 3/2019 | Chin | |
| 2004/0210304 A1 | 10/2004 | Seguin | |
| 2004/0210307 A1 * | 10/2004 | Khairkhahan | A61F 2/2403 623/2.18 |
| 2005/0182483 A1 | 8/2005 | Osborne et al. | |
| 2005/0278023 A1 * | 12/2005 | Zwirkoski | A61F 2/46 623/11.11 |
| 2007/0100435 A1 * | 5/2007 | Case | A61F 2/2475 623/1.24 |
| 2007/0293808 A1 | 12/2007 | Williams | |
| 2008/0249611 A1 | 10/2008 | Melzer | |
| 2009/0105823 A1 * | 4/2009 | Williams | A61F 2/441 623/17.16 |
| 2010/0057192 A1 | 3/2010 | Celermajor | |
| 2012/0265186 A1 * | 10/2012 | Burger | A61B 17/8836 606/41 |
| 2013/0131780 A1 | 5/2013 | Armstrong | |
| 2013/0231736 A1 * | 9/2013 | Essinger | A61F 2/2436 623/2.11 |
| 2014/0018935 A1 | 1/2014 | Wang | |
| 2014/0379074 A1 * | 12/2014 | Spence | A61F 2/2427 623/2.11 |
| 2016/0338834 A1 | 11/2016 | Eckberg | |
| 2017/0056175 A1 | 3/2017 | Chin | |

FOREIGN PATENT DOCUMENTS

| | | |
|---|---|---|
| DE | 19509464 | 6/1996 |
| DE | 19619089 | 11/1997 |
| JP | H05-269192 A | 10/1993 |
| JP | 2001-503657 A | 3/2001 |
| JP | 2002-520087 A | 7/2002 |
| JP | 2013-208458 A | 10/2013 |
| RU | 2332960 C1 | 9/2008 |
| SU | 1507369 | 9/1989 |
| WO | 2007127477 | 11/2007 |

OTHER PUBLICATIONS

International Search Report and Written Opinion for PCT/US2018/037393, dated Sep. 25, 2018, 12 pages.

* cited by examiner

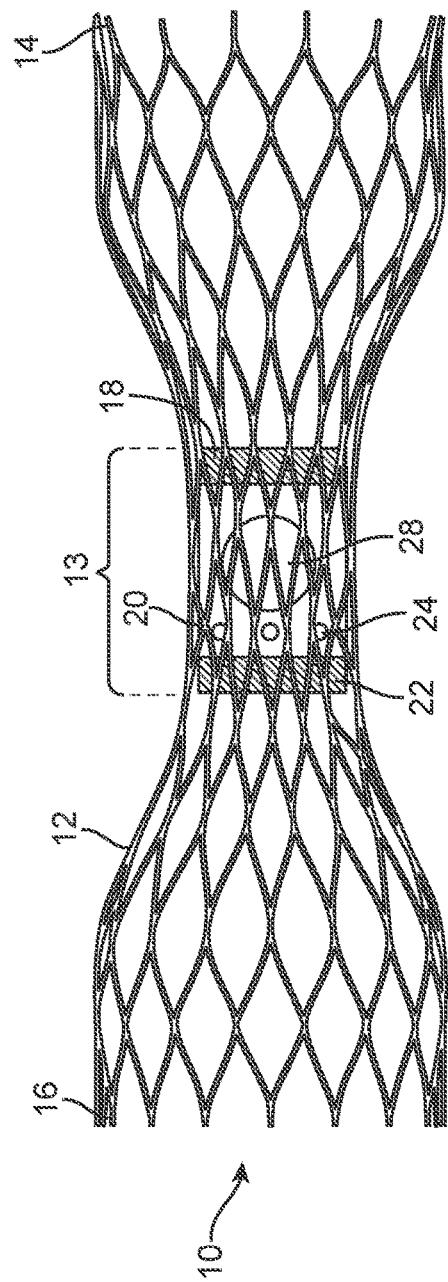
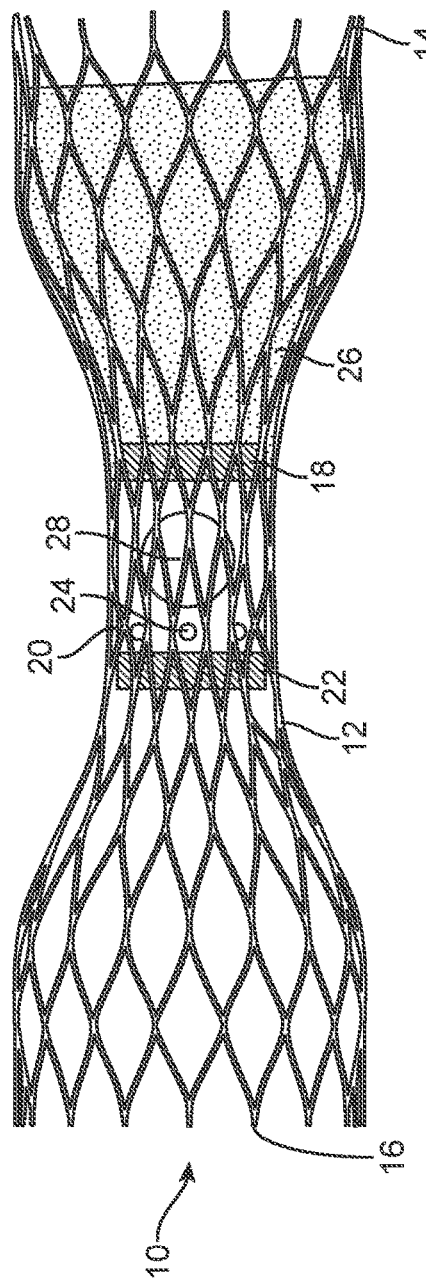
FIG. 1A
FIG. 1B

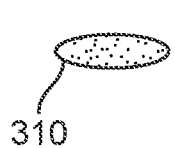
FIG. 8
FIG. 9
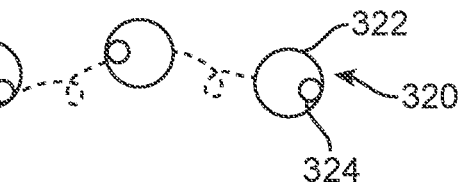
FIG. 10
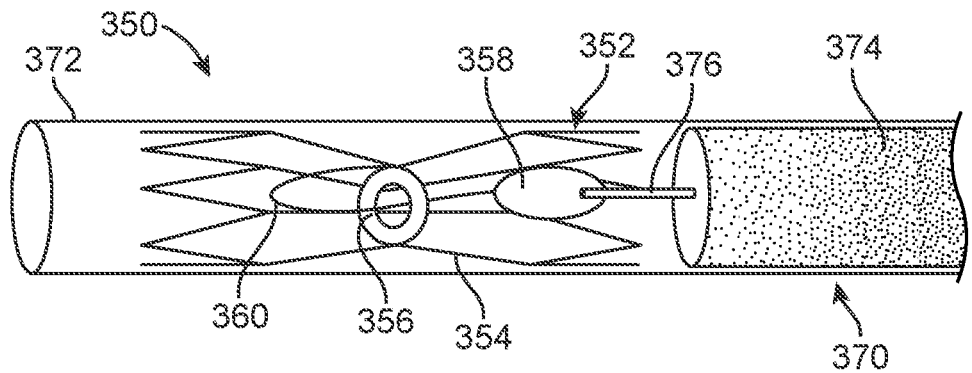
FIG. 11A
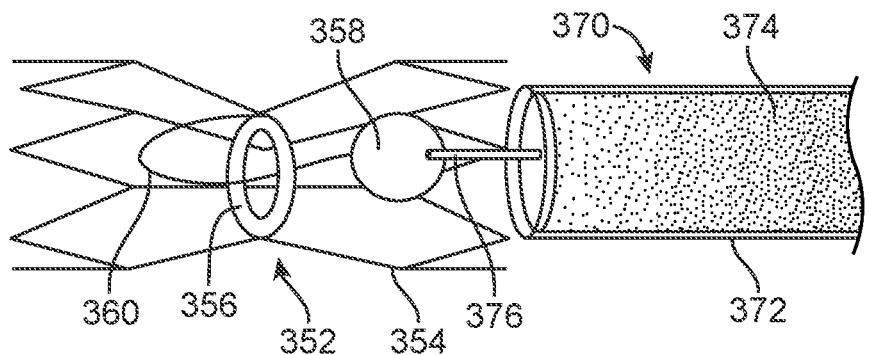
FIG. 11B
FIG. 11C

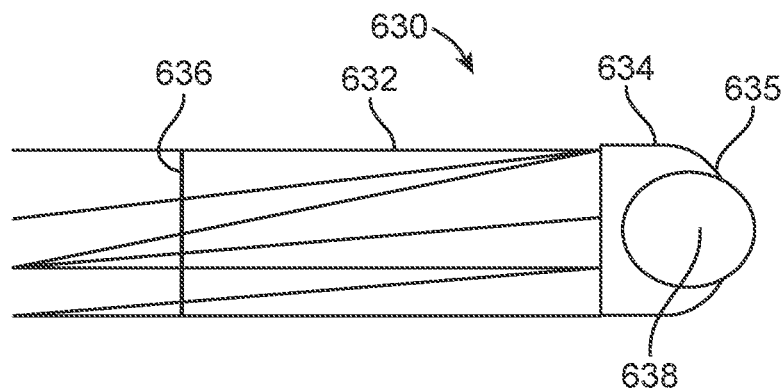
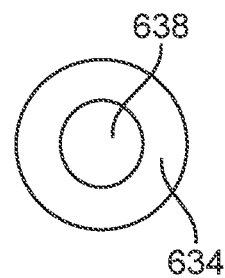
FIG. 31A  FIG. 31B
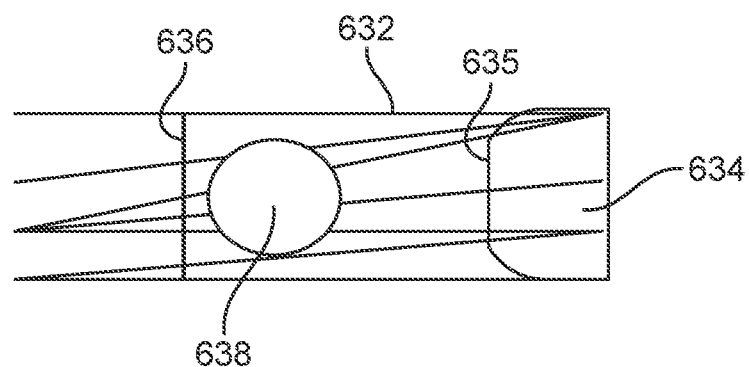
FIG. 31C
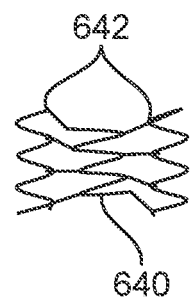
FIG. 32

VASCULAR VALVE PROSTHESIS

CROSS-REFERENCE TO RELATED APPLICATIONS

This application is a continuation-in-part of U.S. application Ser. No. 15/247,523, filed Aug. 25, 2016, entitled, "VENOUS VALVE PROSTHESIS," now U.S. Pat. No. 10,231,838, issued Mar. 19, 2019, which claims priority to U.S. Provisional Application Nos. 62/209,351, filed Aug. 25, 2015 and 62/356,337, filed Jun. 29, 2016, both entitled, "VENOUS VALVE PROSTHESIS." This application also claims the benefit of U.S. Provisional Patent Application Nos.: 62/518,859, filed Jun. 13, 2017, entitled, "VENOUS VALVE PROSTHESIS DEVICE AND METHOD;" and 62/610,338, filed Dec. 26, 2017, entitled, "NEUTRAL DENSITY BALL VALVE." The above-referenced applications are hereby incorporated by reference in their entireties into the present application.

TECHNICAL FIELD

This application relates generally to the field of medical devices. More specifically, the application relates to prosthetic valve implant devices, systems and methods for implantation within the vasculature.

BACKGROUND

Veins in the human body are weak-walled blood vessels that carry blood under low pressures back to the heart from the extremities. To help move the blood toward the heart, most frequently against the force of gravity, veins have one-way valves, which open in the direction of forward-moving blood flow and close to prevent backflow of blood. When these valves become compromised, the veins cannot function properly. Venous disease due to incompetent venous valves is a prevalent clinical problem. In the U.S., 20 million patients demonstrate chronic venous insufficiency, with swelling, pain, and/or ulceration of the affected extremity. An additional 74 million patients exhibit the dilation and deformity of varicose veins.

Various approaches have been advanced for addressing the clinical problem of poorly functioning venous valves. Mauch et al. (U.S. Pat. No. 7,955,346) teach a percutaneous method for creating venous valves from native vein tissue. Laufer et al. (U.S. Pat. No. 5,810,847) describe catheter placement of a clip appliance onto the cusp of a valve to restore the function of incompetent lower extremity venous valves. Multiple designs for implantable venous valves have also been described. These designs involve implantable prosthetic valves that mimic the patient's natural (autologous) valves; that is, the implants use pliable leaflet or flap valves to restore unidirectional venous flow. Examples of such implantable venous valves are described by Acosta et al. (U.S. Pat. No. 8,246,676), Shaolian et al. (U.S. Pat. No. 6,299,637), and Thompson (U.S. Pat. No. 8,377,115), for example.

In order to mimic native human peripheral venous valves, leaflet or flap valves are formed of extremely thin membrane material, to allow the valve to open properly for return flow to occur in the low pressure venous system, while still providing proper sealing and avoiding valvular insufficiency. Prosthetic membrane or flap valves are prone to failure, due to tearing from repeated opening and closing of the leaflets, permanent closure due to thrombosis and cell adhesion to the prosthetic leaflets, or leaflet inversion and incompetence over time. Currently available replacement venous valves, whether artificial or transplanted tissue valves, also often cause problems with thrombosis (clotting) during long term valve implantation.

Therefore, it would be advantageous to have improved implantable venous valve devices. It would desirable, for example, to have a prosthetic venous valve that would prevent and/or accommodate for the occurrence of thrombosis or cell adhesion to the valve components during long term valve implantation. Ideally, the improved prosthetic valve would be relatively easy to implant and would address at least some of the challenges of currently available valve implants discussed above.

BRIEF SUMMARY

The embodiments described herein are directed to implantable, prosthetic vascular valve devices, systems and methods for their use. Typically, the vascular valve implants described herein are used in veins, to replace or do the work of faulty or nonexistent venous valves. However, the implants may be used in arteries or other structures in the human body, such as heart valves or other body lumens that might benefit from a prosthetic valve. Thus, the description herein of venous valve implants may also be applied to arteries and other structures.

In many embodiments, the valve prosthesis device includes a ball valve mechanism to help facilitate blood flow through a vein, artery or other body lumen. The ball valve embodiments generally include an anchoring mechanism, a ball disposed within the anchoring mechanism, and a valve seat against which the ball rests to prevent backflow of blood in a retrograde fashion through the valve. The ball valves also include some type of ball retention mechanism, which prevents the ball from leaving the prosthetic and floating away in the direction of the blood flow. In some embodiments, the mechanism is some kind of blocking member (or members). In other embodiments, the mechanism is some kind of tether. In either case, the ball moves back and forth within the lumen of the anchoring mechanism, between an open position, in which blood flows through the valve and around the ball, and a closed position, in which the ball seats on the valve seat and prevents backflow of blood through the valve. A number of different embodiments of this implantable valve prosthetic device, as well as methods for delivering the device, are described herein.

The vascular valve prosthesis systems described herein generally include a delivery catheter. During placement of an implantable vascular valve prosthesis, it is desirable to minimize the diameter of the delivery catheter used to deploy the valve, to facilitate intravenous access and prosthesis insertion. A smaller diameter delivery catheter is desirable, because it may be inserted into a vein using a smaller puncture hole, and because it decreases trauma to the venous endothelium during advancement and manipulation of the catheter. On the other hand, it is desirable to maximize the diameter of the ball used in the venous valve, as a larger diameter ball may be paired with a valve seat containing a larger diameter valve orifice, to decrease flow resistance through the valve. Enhancing flow characteristics through the valve is important, in order to avoid thrombus (clot) formation in the valve, which may cause valve occlusion. According to various embodiments, the ball within the prosthetic valve may be collapsible/expandable (or "non-rigid"), so that it will change from a smaller diameter configuration during delivery to a larger diameter configuration following implantation. Other embodiments include different or additional mechanisms for preventing clot formation, as will be described further below.

In one aspect of the present application, a venous valve prosthetic implant for treating a vein includes a tubular, expandable anchoring frame, a valve seat formed at or near the middle of the anchoring frame, an expandable ball disposed within the lumen of the anchoring frame, and a ball retention tether attached to the expandable ball and to the valve seat and/or the anchoring frame. The anchoring member may be a stent that extends from a proximal end to a distal end of the implant and forms a lumen from the proximal end to the distal end. The anchoring frame may include a cylindrical proximal portion at the proximal end, a cylindrical distal portion at the distal end, an inwardly angled inlet portion between the cylindrical proximal portion and a middle of the anchoring frame, and an inwardly angled outlet portion between the cylindrical distal portion and the middle of the anchoring frame. The expandable ball expands from a compressed configuration for delivery into the vein through a delivery catheter to an expanded configuration outside the delivery catheter. The expandable ball in the expanded configuration moves between an open position, in which the expandable ball is located apart from the valve seat, to allow forward flow of blood through the implant, and a closed position, in which the expandable ball contacts the valve seat to prevent backflow of blood through the implant.

Some embodiments may further include a material disposed over at least part of the anchoring frame. For example, the material may be made of at least one substance, such as but not limited to polymers, hyaluronic acid, heparin and anticoagulant agents. The anchoring frame may optionally include multiple outward facing protrusions the proximal portion, apart from the proximal end, and/or the distal portion, apart from the distal end. The multiple outward facing protrusions may be barbs, hooks, U-shaped protrusions, V-shaped protrusions or the like. In some embodiments, each of the multiple outward facing protrusions forms an angle with an adjacent portion of the anchoring frame of between 25 degrees and 45 degrees. In some embodiments, the valve seat is a ring attached to at least one of an inner surface or an outer surface of the anchoring member. Alternatively, the valve seat may be formed of material used to make the anchoring frame or of material used to coat or cover the anchoring frame.

In some embodiments, the expandable ball is a solid, compressible foam ball. Such embodiments may optionally further include at least one weight embedded within the ball. Alternatively, the expandable ball may include an elastic shell and a filler substance inside the elastic shell. For example, the filler substance may be air, a gel or a fluid. Some embodiments include at least one weight inside the elastic shell. Optionally, the filler substance may be a curable substance that hardens when cured. In some embodiments, the filler substance is a spiral-cut, elastic, hollow sphere. In some embodiments, the expandable ball includes an aperture through which the ball retention tether is passed. In some embodiments, the expandable ball has a density of less than 2.5 grams per square centimeter. the ball retention tether is attached to the valve seat, wherein the tether and the valve seat form a filling lumen, and wherein the valve seat is accessible through a filling port to pass a filler substance through the valve seat and the tether to fill the expandable ball. In some embodiments, the expandable ball has a density of no greater than 1.06 grams per square centimeter, and the tether is elastic, to pull the ball toward the valve seat to prevent backflow of blood through the implant.

In some embodiments, the inlet portion and the outlet portion each form an angle, relative to a longitudinal axis of the implant, of between 15 degrees and 35 degrees. In some embodiments, the ball retention tether has a length of between 0.5 millimeters and 10 millimeters. In some embodiments, the ball retention tether is long enough to allow the expandable ball to be positioned outside of the distal end of the anchoring frame. In various embodiments, the expandable ball may be made of a material such as but not limited to thermoplastic polyurethane, elastomeric thermoplastic polyurethane, PVC, Polyethylene, polycarbonate, PEEK, ultem, PEI, polypropylene, polysulfone, FEP, PTFE, coated hollow heavy metal or combinations thereof.

In another aspect of the present application, a venous valve prosthetic implant system for treating a vein includes an implant, according to any of the aspects and embodiments described above, and a delivery device. The delivery device includes an elongate, flexible catheter body and a deployment plunger disposed within the catheter body for pushing the implant out of the catheter body.

In some embodiments, the deployment plunger includes a curing member for curing a curable material of which the expandable ball is at least partially made. For example, the curing member may be configured to emit a curing agent, such as but not limited to heat, light, electricity, sound waves, or a chemical mixture. In some embodiments, the delivery device further includes an inflation tube disposed within the catheter body, where the inflation tube includes a distal end configured to enter an aperture in the expandable ball to inflate the expandable ball. In some embodiments, the inflation tube further includes a curing member configured to emit a curing agent. In alternative embodiments, the delivery device may further include an inflation attachment configured for passing fluid through a lumen in at least one of the valve seat or the ball retention tether to inflate the expandable ball.

Optionally, the system may further include a ball extraction device configured to extract the expandable ball from the implant. In one embodiment, the ball extraction device includes a grasper for grasping the expandable ball and a cutter for cutting a tether attaching the expandable ball to at least one of the anchoring frame or the valve seat. In some embodiments, the ball extraction device is configured to pass through the catheter body of the delivery device. The delivery device may also optionally include at least one orientation indicator for indicating an orientation of the implant within the catheter body.

In another aspect of the present disclosure, a method for implanting a venous valve prosthetic implant in a vein or other blood vessel first involves advancing a delivery catheter containing the implant into the vein. The method next involves retracting a catheter body of the delivery catheter and/or advancing a deployment plunger of the delivery catheter, to cause the implant to exit a distal end of the delivery catheter. Then, a tubular stent anchoring member and a ball disposed inside the anchoring member are expanded, within the vein and outside of the delivery catheter. The anchoring member, when expanded, contacts an inner wall of the vein to maintain the implant within the vein. The ball, when expanded, moves between an open position, in which the ball is positioned to allow forward flow of blood through the implant, and a closed position, in which the ball contacts a valve seat, to prevent backflow of blood through the implant. Lastly, the method involves removing the delivery catheter from the vein.

In some embodiments, expanding the anchoring member and the ball involves releasing the anchoring member and the ball from constraint within the catheter body, and both the anchoring member and the ball are made of at least one shape memory material. Some embodiments may further include using the delivery catheter to cure a curable material of which the ball is at least partially made. This curing may involve emitting a curing agent, such as heat, light, electricity, sound waves, or a chemical mixture.

In some embodiments, the method further involves advancing an inflation tube out of the catheter body of the delivery catheter, where a distal end of the inflation tube is positioned through an aperture of the ball, and inflating the ball, using the inflation tube. In various embodiments, the ball may be inflated with air, a fluid, a gel or an elastic, hollow sphere. In some embodiments, inflating the ball involves using an inflation attachment of the delivery catheter to pass fluid through a lumen in a valve seat and/or a ball retention tether of the implant. In some embodiments, the method also includes orienting the implant with the catheter body, using at least one orientation feature on at least one of the implant, the catheter body or a handle coupled with the catheter body.

Optionally, the method may also include extracting the ball from the implant, using a ball extraction device. For example, extracting the ball may involve grasping the ball with a grasper of the extraction device and cutting a tether attached to the ball, using a cutter of the extraction device.

These and other aspects and embodiments are described in further detail below, in reference to the attached drawing figures.

BRIEF DESCRIPTION OF THE DRAWINGS

FIGS. 1A and 1B are side views of a vascular prosthetic valve implant, according to one embodiment;

FIG. 8 is a view of a compressible foam ball of a vascular prosthetic valve implant, according to one embodiment;

FIG. 9 is a view of an elastic, filled ball of a vascular prosthetic valve implant, according to one embodiment;

FIG. 10 is a view of an air filled ball with an internal weight, of a vascular prosthetic valve implant, according to one embodiment;

FIGS. 11A and 11B are side views illustrating a method for delivering a vascular prosthetic valve implant and inflating an elastic ball of the implant, according to one embodiment;

FIG. 11C is a front view of the dual lumen inflation catheter of FIGS. 11A and 11B;

FIGS. 31A-31C are side, front and side views, respectively, of a vascular prosthetic valve implant with a flap valve ball retaining member, according to one embodiment;

FIG. 32 is a side view of an expandable anchoring frame of a vascular prosthetic valve implant, having barbs protruding outward in locations separate from the ends of the frame, according to one embodiment;

DETAILED DESCRIPTION

Figure 2A:
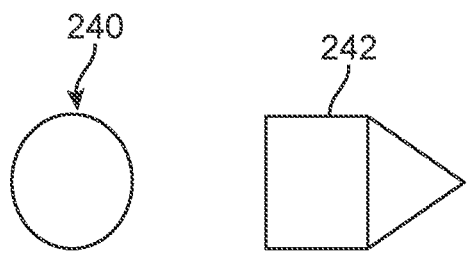
FIGS. 2A-2C are front and side views of three different shapes of balls for a vascular prosthetic valve implant, according to three alternative embodiments.

This application describes various embodiments and features of a device, system, and method involving a vascular valve prosthesis for implantation in a blood vessel to improve function of the blood vessel. In many cases, the vascular valve prosthesis is used in human veins, to help treat venous insufficiency. In alternative embodiments, however, the valve prosthesis may be used in arteries, other locations in the body, such as heart valves or other body lumens, and/or it may be used in animals. Therefore, although the following description focuses on use of the valve prosthesis in veins, this should not be interpreted as limiting the scope of the claims.

Many of the embodiments described herein are of a vascular ball valve prosthesis, as opposed to prior art leaflet or flap valve approaches. The assignee of the present application described a number of embodiments of ball valve prostheses in U.S. Patent Application Pub. No. 2017/0056175, titled "Venous Valve Prosthesis" (hereinafter referred to as "the Venous Valve Prosthesis application"), filed Aug. 25, 2016, the full disclosure of which is hereby incorporated into this application. As mentioned above, some potential challenges with a vascular ball valve include: (1) being able to compress the valve prosthesis into a small-diameter catheter for delivery while also allowing for good flow dynamics through the valve once implanted, (2) preventing clot formation on the ball or other parts of the prosthetic valve, and (3) preventing migration of the valve prosthesis within the vein, due to the increasing diameter of veins as they approach the heart. The embodiments described below address these challenges.

Referring now to FIGS. 1A and 1B, in one embodiment, a prosthetic venous valve implant 10 may include an anchoring member 12 (or "anchor frame"), such as a self-expanding, stent-like frame, for anchoring the implant 10 within a vein. The anchoring member 12 may have a first end 14 (sometimes referred to herein as an "upstream end"), a second end 16 (sometimes referred to herein as a "downstream end"), and a middle valve portion 13. Although not labeled FIGS. 1A and 1B, portions of the anchoring member 12 that lie between the first end 14 and the middle valve portion 13 and between the second end 16 and the middle valve portion 13 may be referred to as an "upstream portion" and a "downstream portion," respectively, of the anchoring member 12. In many embodiments, there is no clear delineation or demarcation between the various portions of the anchoring member 12, and these descriptive terms are used for explanatory purposes only and should not be interpreted as limiting the scope of the invention.

Optionally, as illustrated in FIG. 1B, all or a portion of the anchoring member 12 may be coated or otherwise covered with a material or membrane 26, to help direct blood flow through the implant 10 and prevent blood from flowing through the wall of the anchoring member 12 in the coated portion. In some embodiments, the membrane 26 may be made of or coated with an anticoagulant substance. In alternative embodiments, however, the anchoring member 12 may include no membrane or coating material. This may be possible, for example, in embodiments that expand sufficiently that the native vein wall itself acts as a wall, so that blood is conducted by the vein wall itself. In general, the anchoring member 12 is configured to anchor the valve implant 10 to the luminal surface of the vein.

The venous valve implant 10 may also include a tubular frame 20, which is housed within the anchoring member 12, and a ball 28 housed within the tubular frame 20. Attached to, or integrally formed with, the tubular frame 20 are a valve seat 18, a retention member 22, and multiple through-holes 24, through which blood is free to exit the tubular frame 20. In some embodiments, the tubular frame 20, valve seat 18, retention member 22 and ball 28 may be referred to as the "valve portion" of the implant device 10, which is housed within the anchoring member 12.

In alternative embodiments, which will be described further below, the prosthetic venous valve implant may include fewer parts than in the valve implant 10 of FIGS. 1A and 1B. For example, alternative embodiments do not include a tubular frame. These embodiments may simply include a valve seat attached directly a self-expanding stent anchoring member, a ball, and a ball retention feature, such as a tether or a constraining portion of the anchoring member. Other embodiments may include additional components or features, such as retaining barbs on an anchoring member. A number of these alternative embodiments and features are described in greater detail below.

The ball 28, embodiments of which will be described further below, may be collapsible (or "compressible" or "flexible"), to help allow the valve implant 10 to be compressed and loaded into a small diameter delivery catheter. The density of the ball 28, in some embodiments, may be equal to, approximately equal to, or slightly greater than the average density of venous blood (or arterial blood in other embodiments), so the valve functions with both a low opening pressure and a low closing pressure. For example, in some embodiments, the ball 28 may have a density of between about 1.06 grams per cubic centimeter (approximately the density of blood) and about 2.5 grams per cubic centimeter, or more specifically between about 0.9 and about 2.5 grams per cubic centimeter, or even more specifically, between about 0.9 and about 2.0 grams per cubic centimeter. In alternative embodiments, the density of the ball 28 may fall outside these ranges, such as between about 0.1 grams per cubic centimeter and about 5 grams per cubic centimeter. Various additional ranges of densities for the ball 28 include, but are not limited to between 0.96 and 1.16 grams per cubic centimeter, between 0.7 and 1.42 grams per cubic centimeter, between 0.1 and 1.06 grams per cubic centimeter, between 0.5 and 1.06 grams per cubic centimeter, between 1.06 and 2.5 grams per cubic centimeter, and between 1.06 and 2.0 grams per cubic centimeter.

In various embodiments, the ball 28 may be constructed of any of a number of suitable materials, including but not limited to PTFE (polytetrafluoroethylene), silicone rubber, silastic rubber, silicone, stainless steel, Teflon, thermoplastic polyurethane, elastomeric thermoplastic polyurethane, PVC, Polyethylene, polycarbonate, PEEK, ultem, PEI, polypropylene, polysulfone, FEP, coated hollow heavy metal or any combination thereof. Optionally, an anti-coagulant agent, such as heparin, or another coating, such as hyaluronic acid, may be bonded to the surface of the ball 28. The valve seat 18 may be formed of toroidal elastomer, silicone rubber, or other material.

Figure 2B:
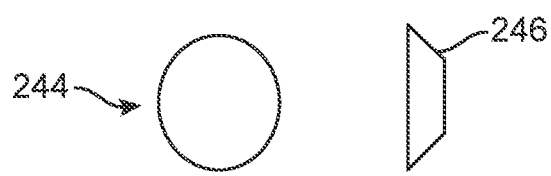
Figure 2C:
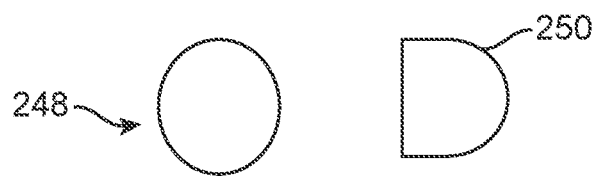

In various alternative embodiments, the ball 28 may have any suitable shape, size, surface feature(s) or the like. In its simplest form, for example, the ball 28 may be spherical and solid. Alternatively, and with reference now to FIGS. 2A-2C, a ball incorporated into a prosthetic valve implant of the present disclosure may have any of a number of alternative shapes, such as ovoid, oblong, asymmetrical, etc. In FIGS. 2A-2C, the left hand view is a front view, and the right hand view is a side view. As illustrated in FIG. 2A, a ball 240 according to one embodiment may have a shape 242, when viewed from the side, of a cylinder with a pointed end. As illustrated in FIG. 2B, a ball 244 according to another embodiment may have a shape 246, when viewed from the side, of a rhombus. As illustrated in FIG. 2C, a ball 248 according to yet another embodiment may have a shape 250, when viewed from the side, of a cylinder with a rounded end. Any other shape may be used, according to alternative embodiments. In some embodiments, the ball 28 may have an outer shell and an inner core, and these two parts may be made of different substances. In some embodiments, the inner core may be made of a liquid substance, and in some embodiments the liquid may be injected through the outer shell to fill the core. The substance may be an anticoagulant or other drug or therapeutic substance and may leak out of one or more holes in the shell in some embodiments. The ball 28 may also have surface features, such as dimples, grooves, indents, pockets or the like. In embodiments, for example, surface features may facilitate the flow of blood around the ball 28. Again, these and other embodiments of the ball 28 will be described more fully below.

Figure 3A:
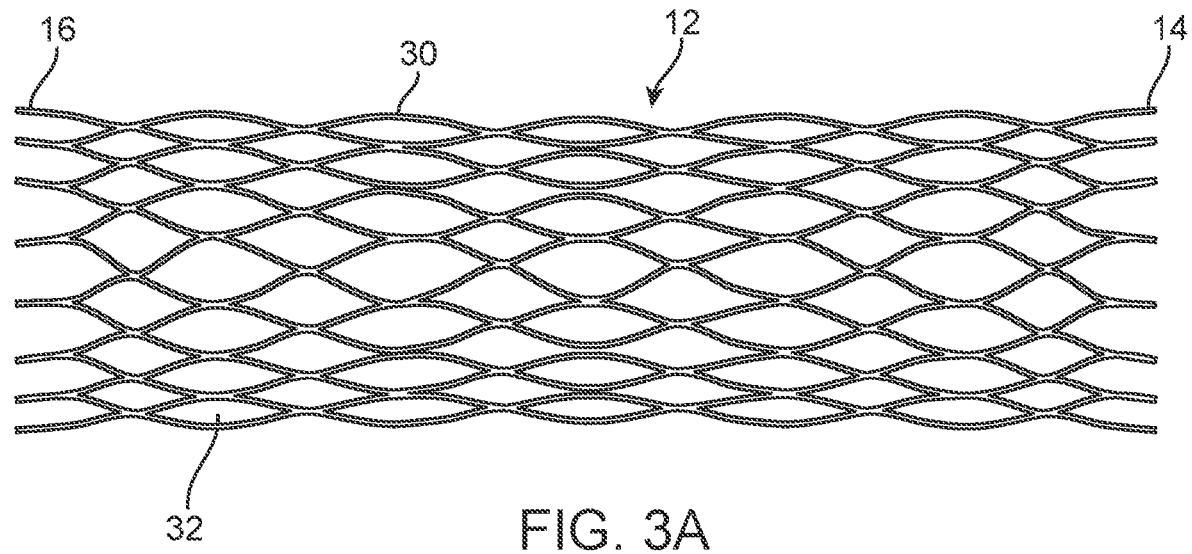
FIGS. 3A and 3B are side views of an expandable anchoring frame of a vascular prosthetic valve implant in its configuration before shaping (FIG. 3A) and after shaping (FIG. 3B), according to one embodiment.
Figure 3B:
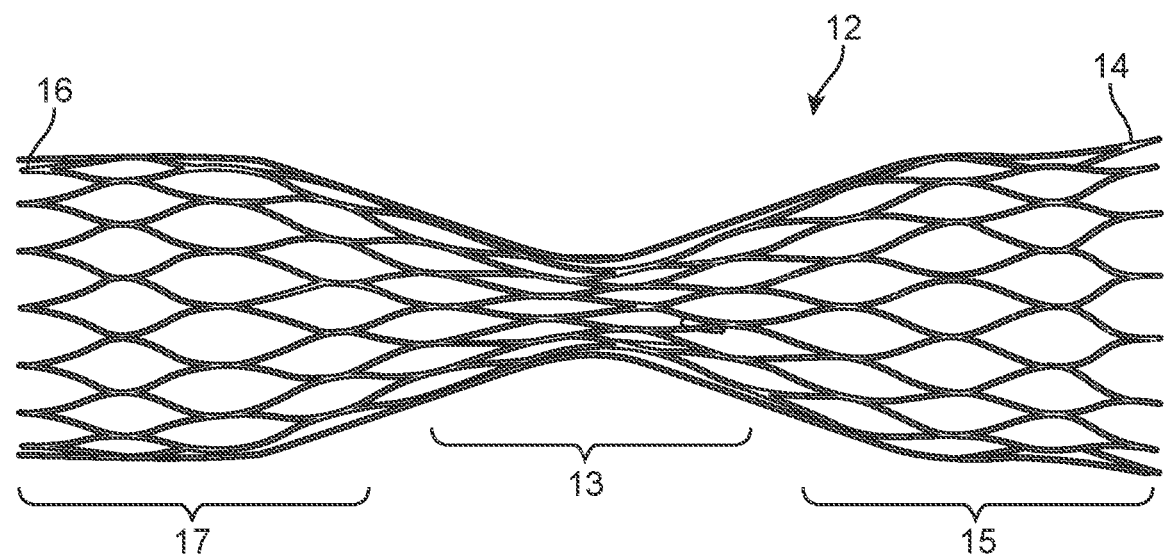

With reference now to FIGS. 3A and 3B, the anchoring member 12 (or "anchoring frame") is illustrated in further detail. In various embodiments, the anchoring member 12 may be formed as a stent-like lattice structure 30, (or sometimes referred to herein simply as a "stent"), with open portions 32 within the lattice. The anchoring member 12 is typically self-expanding, but in alternative embodiments it may be expandable, such as with a balloon catheter. In some embodiments, all or a portion of the self-expanding anchoring frame 12 may be coated, to render it impervious to blood flow. (In other words, so that blood flows through the lumen of the anchoring member 12 and not through the open portions 32.) The anchoring member 12 may be a frame constructed of an engineered polymer (i.e., PEEK, Polypropylene, PTFE, etc.), stainless steel, or a superelastic metal, such as Nitinol. For example, a Nitinol tube may be laser cut in a lattice pattern 30 to form the anchoring member 12.

As illustrated in FIG. 3B, in some embodiments, the middle valve portion 13 of the anchoring member 12 may either not expand or may expand less than (to a smaller diameter than) an upstream portion 15 and a downstream portion 17 of the anchoring member 12. The upstream portion 15 and downstream portion 17 may be expanded, for example, to between 1 mm and 30 mm, and the middle valve portion 13 may be between 1 mm and 30 mm. More specifically, some embodiments may have an upstream portion 15 and a downstream portion 17 that expand to between 10 mm and 20 mm, and a middle valve portion 13 that may be between 2 mm and 10 mm. The length of the anchoring member 12 may be between 1 mm and 200 mm, with some embodiments between 20 mm to 40 mm. The first end 14 and the second end 16 of the anchoring member 12 may have multiple apices, which, when expanded, anchor the anchoring member 12 to the inner wall of the vein. The anchoring member 12 may be heated above its transition temperature and quenched, to place it in its austenitic, self-expanding state.

Referring again to FIG. 1B, in some embodiments, some or all of the open areas 32 of the lattice 30 may be closed off via the membrane 26, which may be a thin layer of silicone rubber or a covering membrane such as PET (polyethylene teraphthalate), PTFE, Nylon, hyaluronic acid or other material. In some embodiments, the membrane 26 may have anticoagulant properties and may thus be referred to herein as an "anticoagulant membrane," but the anticoagulant properties are not required. The membrane 26 may also be referred to in this application as a "hemostatic membrane," because it prevents or helps prevent blood from flowing through the openings 32 in the wall of the anchoring member 12. The membrane 26 may cover the inlet and/or outlet sections of the anchoring member 12 and may thus, when the anchoring member 12 is expanded, form a seal against the inner vein wall, to prevent leakage around the outside of the anchoring member 12. Sealing may also be facilitated by adding short barbs 34 onto the apices first end 14 (or "inlet" or "upstream" end). In various alternative embodiments, barbs 34 may be included on the second end 16, on both the first and second ends 14, 16, on the middle valve portion 13, or on any combination thereof. The first end 14 of the implant 10, with the membrane 26, may form a circumferential linear seal against the inner surface of the vein, facilitated by the barbs 34 protruding into the vein wall. The edge of the membrane 26 may also be thickened with respect to the remainder of the membrane 26, to enhance its sealing capability.

One advantage of the self-expanding venous valve prosthesis 10 is its sealing mechanism, which incorporates a significantly more substantial valve structure—the moveable ball 28 that seats onto the ring of the valve seat 18. Other advantages include the self-expanding frame/anchoring member 12 that distends the vein wall upon deployment, to prevent valve migration, maximize flow-through area, and minimize sheath size for introducing the device 10 and the impermeable covering 26. Use of a ball valve instead of super-thin membranes or leaflets imparts longevity to the implant 10. Due to the larger size and greater mass of the ball 28, compared to thin leaflets, and due to the greater excursion of a rolling ball 28 upon opening and closing of the valve, a ball valve will avoid at least some of the sealing and fatigue problems encountered with thin membrane and leaflet valves. Another advantage of the venous valve implant device 10 is that it is able to clean itself, at least in part, as the ball 28 rolls back and forth and thus cleans off the inner surface of the anchoring member 12, the valve seat 18 and/or the retention member 22. To provide adequate excursion of the rolling ball 28 for the purpose of self-cleaning the device 10, the distance between the valve seat 18 and the retention member 22 may be about two to four times greater than the diameter of the ball 28. In alternative embodiments, this distance may be longer or shorter, such as about 1.5 to about five times greater than the diameter of the ball 28, for example. As the ball 28 moves back and forth, it rubs against the inside of the ball valve frame 20, dislodging potential adherent cells and thrombus. In embodiments described further below that do not include a tubular frame 20, the ball 28 may instead clean an inner surface of the anchoring member 12.

Figure 4A:
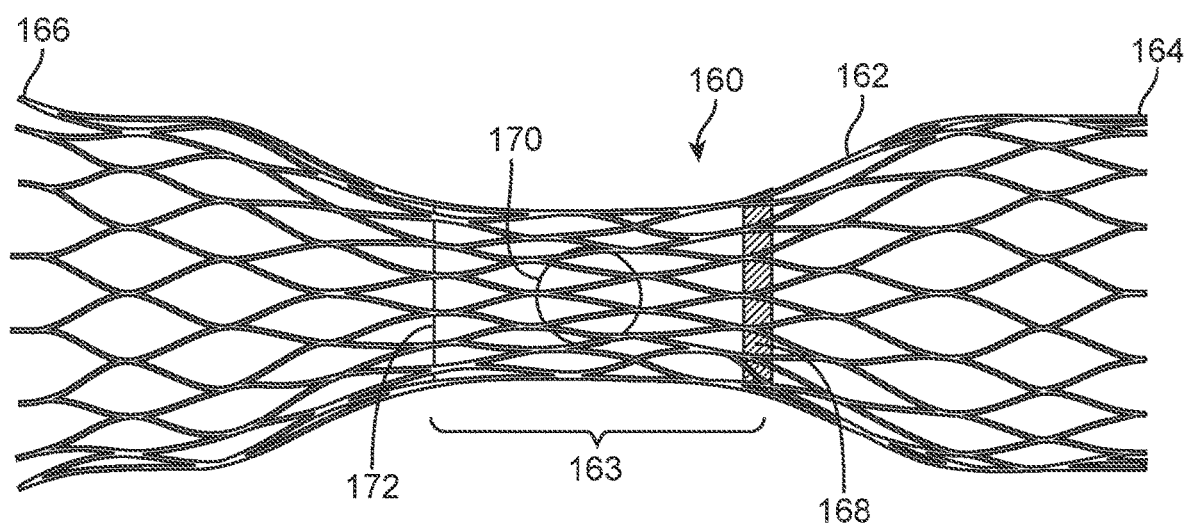
FIGS. 4A and 4B are side and front views, respectively, of a vascular prosthetic valve implant, according to one embodiment.
Figure 4B:
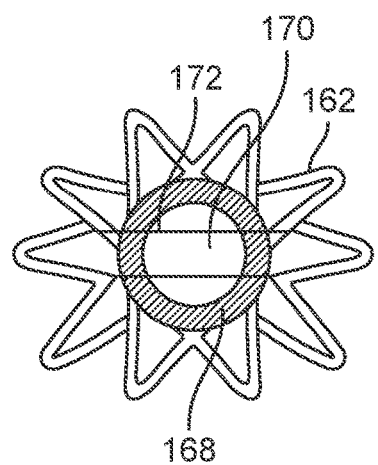

Referring now to FIGS. 4A and 4B, in another embodiment, a venous valve prosthesis 160 may include an anchoring member 162 (or "anchoring frame"), with a first end 164, a second end 166, and a middle valve portion 163. Inside the anchoring member 162 are a ball 170, a valve seat 168 and a ball retention member 172. In this embodiment, there is no inner tubular frame. Instead, the first and second ends 164, 166 of the anchoring member 162 expand to anchor the implant 160 within a vein, and the middle valve portion 163 maintains a smaller diameter and acts as a substantially tubular holder for the ball 170. As discussed above, the anchoring frame 162 may be made of continuous superelastic material, such as Nitinol, which may be entirely or partially coated in a material, such as PTFE, silicone, or hyaluronic acid. This coating funnels blood through the central valve component. The ball retention member 172 may include multiple pieces of crossing suture, which extend across the lumen of the implant in any suitable pattern or configuration. The entire implant 160 may be compressible (ball 170, valve seat 168, anchoring frame 162, ball retention member 172), so that it can be packed into a small delivery catheter to facilitate ease of implantation. Any valve seat, ball, anchor feature such as barbs, or retainer embodiment described in this application may be used in this embodiment. External compression and/or a ferromagnetic ball and externally placed magnet may also be applied with this embodiment, for clearance of clot. Removal of the entire device 160, or just the ball 170, is also possible. The same deployment funnel may be mated with the proximal end of the prosthesis 160, using the graspers or small scissors to cut the retention member 172, and using graspers or suction to remove the ball 170 from the valve 160.

In some embodiments, the ball 170 may have a ball diameter such that the distance between the valve seat 168 and the ball retention member 172 is between two times and four times greater than the ball diameter. The ball diameter may also be sized such that the ball 170 contacts an inner surface of the middle valve portion 163 as the ball 170 travels back and forth between the valve seat 168 and the ball retention member 172, so that contact between the ball 170 and the middle valve portion 163 is able to dislodge substances that form on or cling to the middle valve portion 163. This sizing of the ball 170 and the diameter of the middle valve portion 163 thus may impart a "self-cleaning" ability to the implant device 160. For example, in some embodiments, the ball 170 may have a diameter of between 0.5 mm and 30 mm. More specifically, in some embodiments, the ball 170 may have a diameter between 1 mm and 8 mm.

The valve seat 168 may be formed of toroidal elastomer, silicone rubber, Nitinol, or any other material. In some embodiments, the valve seat 168 and the anchoring frame 162 may be made of the same material, such as Nitinol in one embodiment. The valve seat 168 may be rigid (e.g., stainless steel, Nitinol, or polycarbonate) or flexible/collapsible (e.g., silicone), to facilitate packing into a smaller delivery sheath. In some embodiments, an inner surface of the valve seat 168 may be coated in the same continuous material lining of the anchoring member 162, to limit or prevent luminal or blood exposure. The valve seat 168 may expand to a diameter greater than that of the delivery sheath and/or vein wall to maximize flow-through area. The valve seat 168 may be permanent or replaceable.

As mentioned above, the anchoring member 162 may be a self-expanding or balloon expandable anchoring frame, having a stent-like lattice structure. In this embodiment, the first or upstream end 164 and the second or downstream end 166 expand to greater diameters than the middle valve portion 163 of the anchoring member 162. The two ends 164, 166 typically dilate a vein or other vessel into which they are implanted. In some embodiments, the middle valve portion 163 also expands upon delivery to a diameter sufficient to dilate the vein. In some embodiments, the implant 160 also includes a material, membrane or coating (not illustrated), disposed over part of the anchoring member 162. This coating may act as a hemostatic barrier that funnels blood through the central lumen of the device 160. The coating may consist of a hemostatic material, such as a polymer (e.g. PTFE, silicone, PET, nylon, or hyaluronic acid), and may further be infused or bonded with heparin, hyaluronic acid, or other agent. The hemostatic membrane covering the inlet and/or outlet sections of the anchoring frame 162 can seal against the inner vein wall to prevent or reduce leakage around the outside of the implant 160. Additionally, the extreme downstream end 166 may expand to a slightly larger diameter than an immediately adjacent downstream portion, thus forming a wider expandable portion, which may also be uncovered/uncoated and may act as multiple anti-migration tips when the anchoring member 162 is expanded. These tips may help prevent downstream migration of the implant 160 within a vein. Optionally, some embodiments may include additional anti-migration barbs on the anchoring frame 162.

The anchoring member 162 may be a frame constructed of an engineered polymer (i.e., PEEK, Polypropylene, PTFE, etc.), stainless steel, or a superelastic metal, such as Nitinol. A Nitinol tube may be laser cut in a lattice pattern, and its proximal and distal sections (or "downstream and upstream sections," respectively) may be expanded, while the middle valve portion 163 may be retained in a smaller diameter. In some embodiments, the proximal and distal sections of anchoring member 162 may be expanded to between 0.1 mm and 100 mm. More specifically, some embodiments may have proximal and distal sections expanded to between 10 mm and 20 mm. In some embodiments, the length of the anchoring member 162 may be between 1 mm and 200 mm, with some embodiments between 20 mm to 40 mm. In some embodiments, the central narrowed middle valve portion 163 may have a diameter between 1 mm and 100 mm, and a length between 0.1 mm and 100 mm. More specifically, in some embodiments the middle valve portion 163 may have an outer diameter between 3 mm and 20 mm, and a length between 5 mm and 15 mm. The anchoring member 162 may be self-expandable from a collapsed configuration, for delivery through a delivery catheter, and have an expanded configuration upon release from the delivery catheter. Alternatively, the anchoring frame 162 may be balloon expandable. The upstream end 164 and the downstream end 166 of the anchoring frame 162 may be sized to dilate the vein when the implant 160 is implanted in the vein. The middle valve portion 163 of the anchoring frame may also be sized to dilate the vein when the implant 160 is implanted in the vein. The middle valve portion 163 may have a mostly straight configuration, as in FIG. 4A, or may have an hourglass shape.

Figure 5:
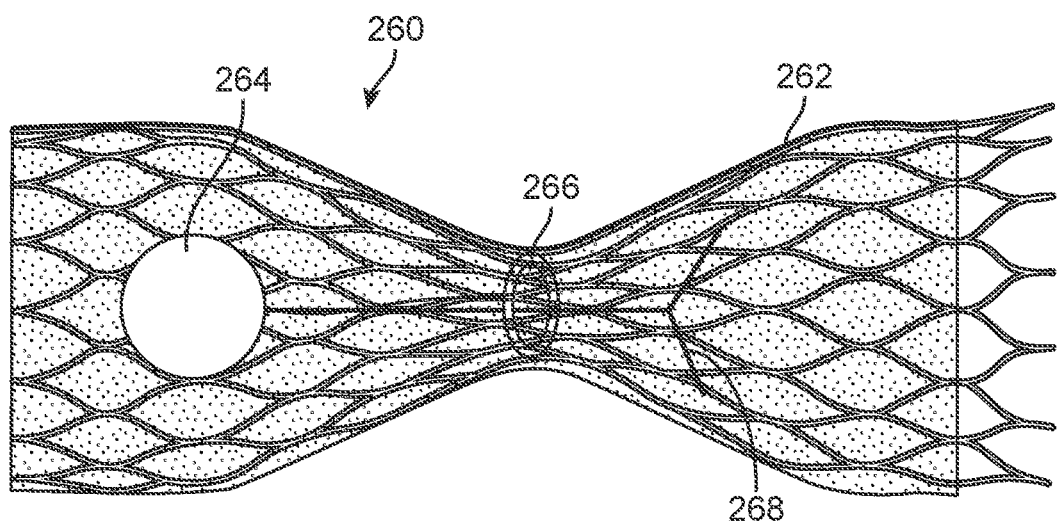
FIG. 5 is a side view of a vascular prosthetic valve implant having a V-shaped ball retaining member, according to one embodiment.
Figure 6:
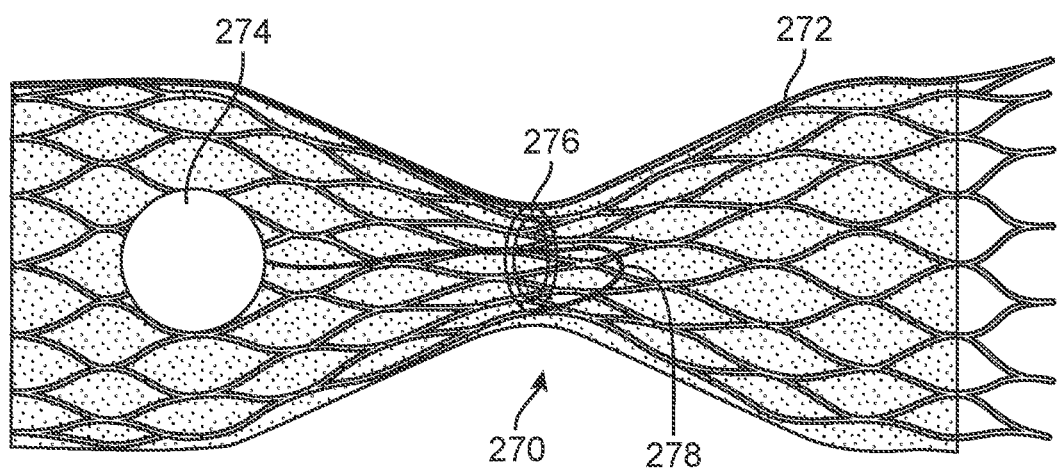
FIG. 6 is a side view of a vascular prosthetic valve implant having a tether, according to one embodiment.

FIGS. 5 and 6 illustrate two additional alternative embodiments of a prosthetic venous valve implant. In the embodiment of FIG. 5, the venous valve implant 260 includes an anchoring member 262, a ball 264, a valve seat 266, and a retention member 268. In this embodiment, the retention member 268 is an expandable wire anchor, attached to the ball 264. The expandable wire anchor retention member 268 may be made of a shape-memory material, for loading into a delivery catheter, and it includes a first end attached to the ball 264 and a V-shaped end opposite the ball 264. The V-shaped end is large enough, when expanded, to not fit through the valve seat 266, thus preventing the ball 264 from passing out of the valve implant 260 in the downstream direction. The end of the retention member 268 attached to the ball 264 may be attached via adhesive, by being passed into or through an aperture in the ball 264 and then being tied, by being welded to the ball 264, or by any other suitable means. In alternative embodiments, the V-shaped end may have other shapes. The valve implant 260 may include any of the features described above, such as a material disposed over all or part of the anchoring member 262, a collapsible valve seat 266, barbs protruding from the anchoring member 262 and/or the like.

In the embodiment of FIG. 6, the implant 270 includes an anchoring member 272, a ball 274, a valve seat 276, and a retention member 278. In this embodiment, the retention member 278 is a tether, attaching the ball 274 to the valve seat 276. The retention member 278 may be made of suture, wire such as Nitinol, an elastic material or the like. Again, the tether retention member 278 stops the ball 274 from passing out of the valve implant 270 in the downstream direction. The end of the retention member 278 attached to the ball 274 may be attached via adhesive, by being passed into or through an aperture in the ball 274 and then being tied, by being welded to the ball 274, or by any other suitable means. The opposite end of the tether retention member 278 may be attached to the valve seat 276, as shown, to the anchoring member 272, or both. The valve implant 270 may include any of the features described above, such as a material disposed over all or part of the anchoring member 272, a collapsible valve seat 276, barbs protruding from the anchoring member 272 and/or the like. Either of these two retention members 268, 278 may be applied in other embodiments described herein.

Figure 7A:
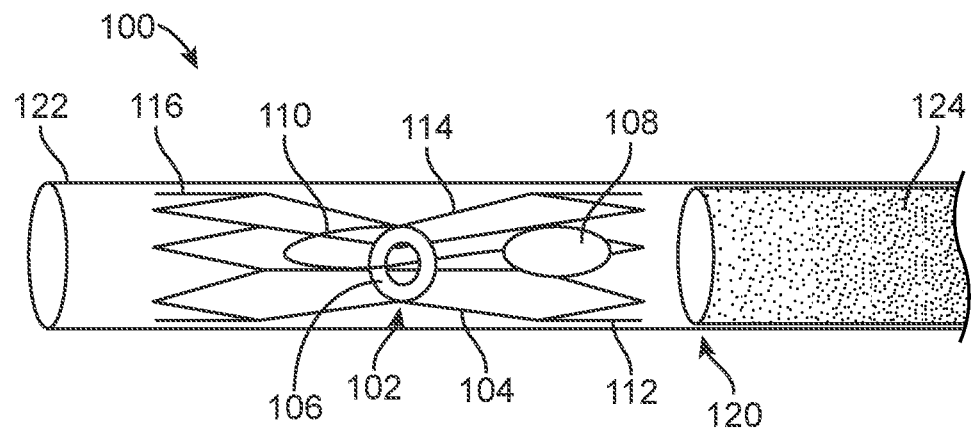
FIGS. 7A and 7B are side views of a vascular prosthetic valve implant system, illustrating delivery of the implant out of the delivery device, according to one embodiment.
Figure 7B:
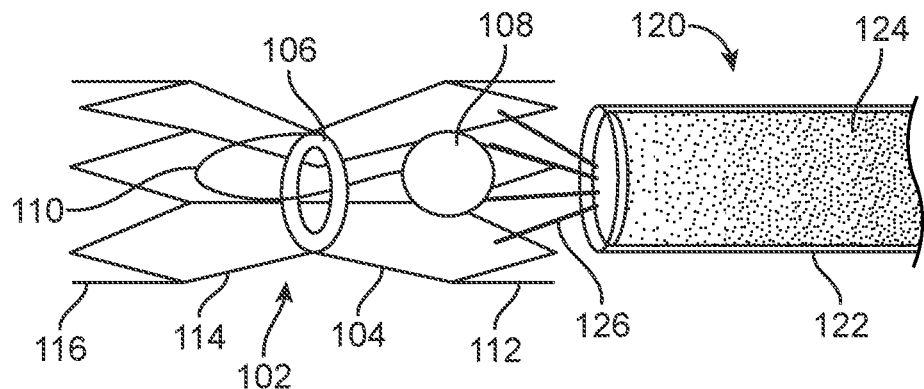

FIGS. 7A and 7B are diagrammatic illustrations of one embodiment of a vascular ball valve prosthetic system 100, which includes the prosthetic vascular valve 102 (or "implant") itself and a delivery catheter 120 for delivering the prosthetic valve 102 to its target location in a vein (or alternatively in an artery). FIGS. 7A and 7B, as well as many of the remaining figures in this application, include diagrammatic representations of different embodiments of a vascular prosthetic valve and a delivery catheter for delivering the valve into a vein (or other blood vessel in other embodiments). In any of these illustrated embodiments, the prosthetic valve may be the same as, or similar to, any of the embodiments described above, in reference to FIGS. 1A-6, or any of the embodiments described in any of the references previously incorporated by reference. Any features, elements or components described for the valve prosthesis embodiments described above or described in any of the references previously incorporated by reference may be applied to the embodiments that follow. Therefore, the size, shape and features of the embodiments described via diagrammatic illustrations should not be limited by the nature of the illustrations themselves.

Returning to FIGS. 7A and 7B, FIG. 7A illustrates the prosthetic valve 102 in a collapsed or compressed configuration, within the delivery catheter 120, and FIG. 7B shows the prosthetic valve 102 in an expanded configuration, outside the delivery catheter 120 (as it might look inside a vein). In this embodiment, the prosthetic valve 102 includes an expandable anchoring frame 104 (or "anchoring member"), which includes a wide proximal portion 112, a wide distal portion 116 and a narrower middle portion 114. The narrower middle portion 114 includes an inwardly angled proximal portion, between the wide proximal portion 112 and the middle of the anchoring frame 104, and an inwardly angled distal portion, between the wide distal portion 116 and the middle of the anchoring frame 104. The valve 102 also includes a valve seat 106 attached to the middle of the anchoring member 104, a ball 108, and a tether 110 attached at one end to the valve seat 106 (and/or the anchoring frame 104 in alternative embodiments) and at an opposite end to the ball 108. The delivery catheter 120 includes a tubular catheter body 122 and a deployment plunger 124 slidably disposed inside the catheter body 122. In some embodiments, a light source (not visible) may be disposed inside, or at the distal end of, the plunger 124, to emit light 126, which will be described further below.

Many of the features and aspects of the implant 102 are described more fully in the Venous Valve Prosthesis Application, which was previously incorporated by reference. In various embodiments, the anchoring frame 104 is formed as an expandable stent. The anchoring frame 104 is a one-piece structure that extends from one end of the implant 102 to the opposite end of the implant 102. The anchoring frame 104 may have any suitable size and shape, some variations of which will be shown and described further below. The anchoring frame 104 may be made of any expandable or self-expanding material and is configured, when expanded, to anchor the implant 102 within the vein being treated. The anchoring frame 104 may be made of any shape-memory metal or polymer, for example, such as Nitinol. In some embodiments, at least a portion of the anchoring frame 104 is coated or covered with a material that may be fully or partially impermeable to blood. Examples of such materials include polymers, hyaluronic acid, heparin and/or anticoagulant agents.

In use, the delivery catheter 120 is advanced into the target vein with the prosthetic valve 102 loaded in the catheter body 122 (FIG. 7A). Once in the appropriate vessel location, the catheter body 122 may be retracted relative to the deployment plunger 124 to cause the valve 102 to exit the catheter body 122 (FIG. 7B). Alternatively, the plunger 124 may be advanced, while the catheter body 122 is held immobile, or a combination of advancement of the plunger 124 and retraction of the catheter body 122 may be employed. Once released, the anchoring member 104 expands to anchor against the blood vessel inner wall. As the anchoring member 104 expands during and after deployment, the compressive force it places on the expandable ball 108 in the compressed configuration inside the catheter body 122 is removed. The ball 108 thus expands to assume its default spherical shape. In some embodiments, as illustrated in FIG. 7B, the deployment plunger 124 may emit light 126 to cure a curable substance of which the ball 108 is at least partially made. The curing process may make the ball 108 harder or more resistant to compression, thus preventing it from accidentally squeezing through one end of the anchoring member 104 after deployment. In alternative embodiments, the ball 108 may be cured via other methods, such as but not limited to the application of sound, heat or electricity to the ball 108. In other embodiments, curing is not used.

The embodiment illustrated in FIGS. 7A and 7B may be referred to as a self-expanding embodiment, in that the anchoring member 104, the ball 108 and the valve seat 110 all self-expand from a compressed, delivery configuration to an expanded, deployed configuration. In alternative embodiments, one or more of these three components (the anchoring member 104, the ball 108 and the valve seat 110) may be expandable but not self-expanding. For example, the anchoring member and the valve seat 110, in one embodiment, may be expanded with the use of a balloon catheter or other expanding device. Although this increases complexity of the delivery and deployment procedure, it may be part of some alternative embodiments. Unless stated otherwise, however, the embodiments described herein are assumed to be self-expanding and thus the anchoring member 104, the ball 108 and/or the valve seat 110 self-expand when released from constraint within the delivery catheter 120.

The expandable ball 108 has a number of different alternative embodiments, some of which are described below. Generally speaking, the various embodiments of the expandable ball 108 may be categorized as either self-expanding or expandable. The self-expanding embodiments of the ball 108 are made at least partially of a resilient or shape-memory material, such as a compressible foam, an elastic shell filled with gel or fluid, or other embodiments, some of which are described below. The expandable (non-self-expanding) embodiments of the ball 108 typically involve some kind of inflation or other expansion mechanism, as described further below.

The valve seat 106 in the embodiment of FIGS. 7A and 7B is compressible, as evident from comparing the two figures, and it may have any of the materials and characteristics described above for valve seats. For example, the valve seat 106 may be formed of silicone rubber, a flexible polymer, such as Viton, a shape-memory metal, such as Nitinol, or any other suitable material. It may be insert-molded into or otherwise attached to an inner surface and/or an outer surface of the anchoring member 104.

Referring to FIGS. 8-10, three different embodiments of a compressible ball for a vascular prosthetic valve are illustrated. In each embodiment, the compressibility of the ball allows it to reside within the compressible anchoring frame of the vascular valve prosthesis in an elongated configuration and then expand to a spherical geometry following valve deployment in the vein.

In one embodiment, depicted in FIG. 8, a vascular valve prosthesis ball 300 may be constructed of closed cell polymeric foam, such as polyurethane foam. The foam ball 300 may be stored inside the valve anchoring frame and delivery catheter in a compressed condition, and expand to a spherical configuration following valve deployment. Optionally, the foam material may be covered in a shell of another material, such as PTFE, silicone, or the like, which acts as a barrier between blood and the foam material. As mentioned previously, in various embodiments, the ball 300 may have any of a number of suitable densities, which may be greater than, equal to or less than the density of blood. The various density ranges and ball materials are listed above and thus are not repeated here.

As illustrated in FIG. 9, an alternative embodiment of a compressible ball 310 may include a hollow spherical shell 312 constructed of an elastic material, such as silicone rubber or polyurethane, filled with a filler substance 314, which may be a fluid, gel or air. The filler substance 314 may be selected such that the overall density of the ball 310 is slightly higher than the density of blood, such that gravity causes the ball 310 to rest against the valve seat to close the valve, but a low forward pressure is sufficient to open the valve, resulting in a low cracking pressure of the valve.

As illustrated in FIG. 10, in another alternative embodiment, the ball 322 may also include an elastic shell 322, in this case filled with air, but also including a small diameter inner weight 324, constructed of material such as stainless steel. The dimensions of the inner weight 324 may be selected to give the ball 320 a desired overall density. Upon movement of the ball 320 towards and away from the valve seat, the weight 324 drops within the ball 320, causing the ball 320 to rotate in an asymmetrical fashion within the valve frame. The asymmetrical contact of the ball 320 against the valve frame may help prevent cell and thrombus adhesion to the ball 320 and thus may help prevent valve occlusion.

In other alternative embodiments, the ball of a vascular valve prosthesis may be constructed of, or filled with, any other suitable combination of foam, fluid, gel, gas, or solid. The combination of filler materials may be selected such that the overall density of the ball is slightly higher than the density of blood. It may further be formed such that it has asymmetrically distributed weight or altered shape that encourages ongoing ball movement and limits stagnation. Further, the material may be selected such that it solidifies or cures around the temperature of blood. This would allow the ball to deform while being compacted for delivery, but subsequently expand and then solidify after deployment once in the presence of blood. Any of the various compressible ball embodiments described in relation to FIGS. 8-10 or in any other figures may be used in any of the vascular valve prosthesis embodiments described herein.

Referring now to FIGS. 11A and 11B, another embodiment of a vascular valve prosthesis system 350 includes an implantable prosthetic valve 352 and a delivery device 370. The valve 352 includes an anchoring frame 354, a valve seat 356, a collapsible ball 358 and a tether 360 attaching the ball 358 to the valve seat 356. The delivery device 370 includes a catheter body 372, a deployment plunger 374 and an inflation catheter 376 attached to the ball 358. The ball 358 may be an inflatable balloon (or "inflatable outer shell"), which is inflated with an inflation fluid. The fluid, in some embodiments, may be curable and thus hardens after curing. The inflatable balloon can exist in an un-inflated state during valve delivery (FIG. 11A), to be inflated with fluid, gel, or gas (FIG. 11B) and then, in some embodiments, cured after valve deployment. Alternatively, the balloon may be pre-filled with curable fluid, gel, or gas, which is then cured and solidifies after deployment. The fluid, gel, or gas may be cured by injecting a curing agent. It may be cured via heat, light (e.g., blue light or UV light), electricity, sound waves, chemical mixture, or other curing method. The curable fluid may be liquid silicone rubber, liquid polyurethane foam, an adhesive, such as epoxy or ultraviolet curing adhesive, or other curable material.

FIG. 11C is a front, cross-sectional view of the inflation catheter 376 illustrated in FIGS. 11A and 11B. In this embodiment, the inflation catheter 376 is a double-lumen catheter, with a light lumen 378 housing a fiber-optic cable to transmit light and an inflation lumen 380 used for fluid injection into the ball 358. In alternative embodiments, the light lumen 378 may be used for any other curing devices and methods.

FIGS. 12A-12E illustrate one embodiment of a method for inflating and curing the ball 358 using the inflation catheter 376. Providing further detail, the inflation catheter includes an outer sheath that lies coaxially over the double lumen catheter body. The outer shell of the ball 358 includes a self-sealing valve that protrudes into the inside of the ball 358, leaving a smooth surface on the outside of the ball 358 for proper sealing against the valve seat 356. The self-sealing valve may be a cylindrical plug of elastomeric material with a collapsed central channel that is sealed to gas or fluid pressure within the balloon.

Figure 12A:
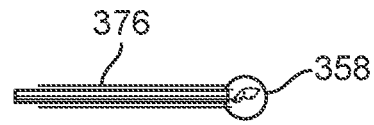
FIGS. 12A-12E are side views illustrating a method for inflating an elastic ball of a vascular prosthetic valve implant, according to one embodiment.
Figure 12B:
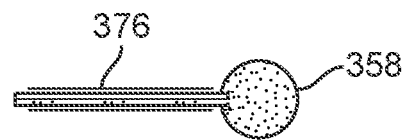
Figure 12C:
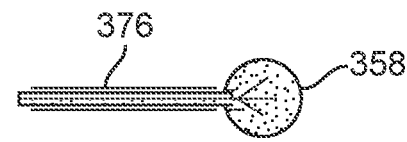
Figure 12D:
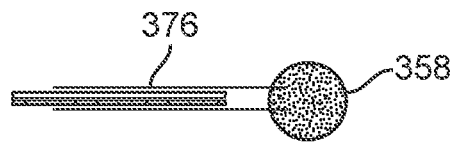
Figure 12E:
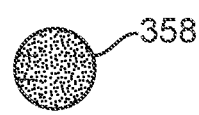

According to this method embodiment, FIG. 12A illustrates insertion of the catheter 376 into the self-sealing valve of the ball 358. In FIG. 12B, the ball 38 is then inflated with inflation fluid to a desired diameter, without detachment of the ball 358 from the catheter. In this embodiment, the ball 358 is inflated with light curing adhesive fluid via the fluid injection lumen 380 of the inflation catheter 376. As in FIG. 12C, following inflation of the ball 358 to the desired volume, light is transmitted via the fiber-optic cable lumen 378, to solidify the fluid inside the ball 358. In FIG. 12D, detachment of the ball 358 is performed by pulling the catheter body of the inflation catheter 376 out of the ball 358 while the outer sheath of the inflation catheter 376 is held stationary to support the ball 358 during catheter withdrawal. Instead of a fiber-optic cable, the second channel could be used to transmit heat, sound waves, electricity, and/or a chemical that reacts with the chemical from the other channel to cure it. Finally, as in FIG. 12E, the ball 358 is inflated, cured and detached from the inflation catheter 376.

Referring back to FIG. 11A, in alternative embodiments, the inflation catheter 376 (and/or a separate curing catheter) may be pre-attached to the ball 358 and loaded into the delivery device 370 with the ball 358 in its collapsed configuration. The inflation catheter 376 may then be used to inflate and cure the ball 358 after deployment out of the delivery device 370. Alternatively, the ball 358 may be pre-filled with curable fluid and still be collapsible for delivery, so that the catheter 376 could instead be a single-lumen catheter designed for curing only (not inflation), via delivery of light, chemical, sound, etc. In either situation the fluid can be cured via heat, light, electricity, sound waves, chemical mixture, or other method, as described above.

Alternatively, the ball 358 could be made of a material or thickness that is less deformable once filled with any fluid, gel, or gas. The ball 358 could be left empty during loading and deployment to allow for a small catheter size, but after deployment filled with material using a catheter channel. This fluid does not need to be a curable fluid, but rather once sufficient fluid is injected into the ball 358, the pressure causes it to retain its desired shape.

FIGS. 13A-13D illustrate an alternative embodiment of a vascular prosthetic valve system 400, including a prosthetic valve 402 and a delivery device 420. As in previously described embodiments, the prosthetic valve 402 includes an anchoring frame 404, a valve seat 406, a collapsible ball 408 and a tether 410. The delivery device 420 includes a catheter body 422, a deployment plunger 424, and an inflation attachment 426 attached to the deployment plunger 424. The inflation attachment 426, which in various embodiments may include one arm or multiple arms, extends over a portion of the anchoring frame 404 during delivery. The inflation attachment 426 has an inner lumen, which is in fluid communication with a lumen in the valve seat 406 and the tether 410, which in turn leads into an interior of the ball 408. Thus, inflation fluid may be passed through the inflation attachment 426, the valve seat 406, and the tether 410 to inflate the ball 408.

Figure 13A:
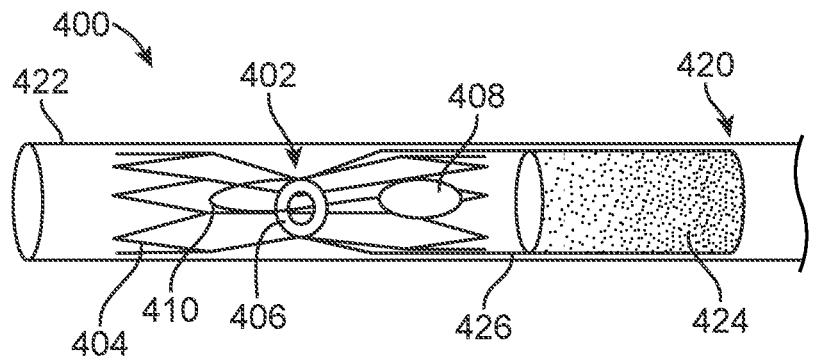
FIGS. 13A-13D are side views illustrating a method for delivering a vascular prosthetic valve implant into a blood vessel, according to one embodiment.
Figure 13B:
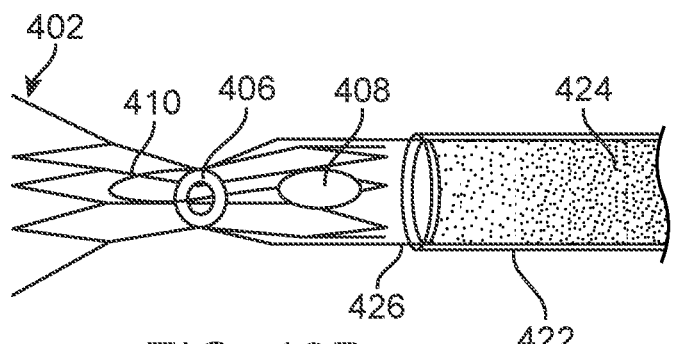
Figure 13C:
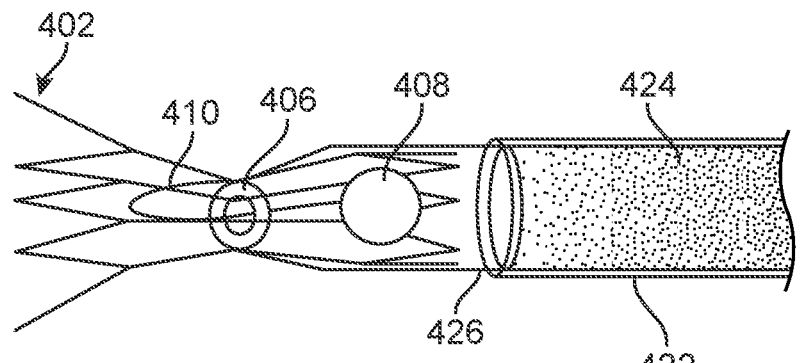
Figure 13D:
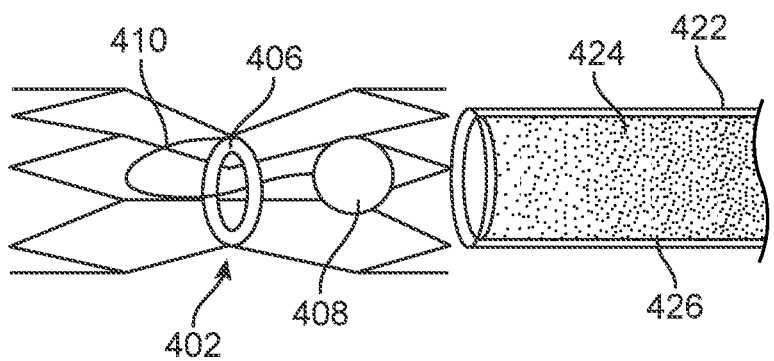

FIG. 13A shows the prosthetic valve 402 fully inside the delivery device 420 for delivery into the vein or other blood vessel. As shown in FIG. 13B, the catheter body 422 may be retracted, allowing a first portion of the anchoring frame 404 to expand inside the vein. As illustrated in FIG. 13C, inflation fluid may then be passed through the inflation attachment 426, the valve seat 406, and the tether 410 to inflate the ball 408. Optionally, the ball 408 may be cured, using any of the curing methods listed above or any other suitable curing method. Then, as in FIG. 13D, the inflation attachment 426 is retracted. As mentioned above, the inflation attachment 426 may have one arm or prong, or it may have multiple arms or prongs. One of the prongs, or multiple prongs, may have a single or double lumen, as described above. In a single lumen approach, fluid can be injected to distend the ball 408 to the desired shape where outward pressure is sufficient to prevent distortion and potential movement through the valve seat 406. Alternatively, the ball 408 can be pre-filled with a curable agent. The single lumen can then be used to transmit a curing agent such as light.

Figure 14A:
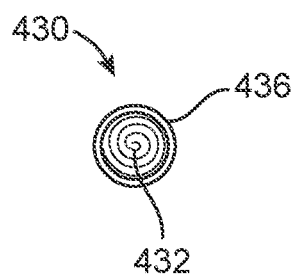
FIG. 14A is a cross-sectional view of a ball of a vascular prosthetic valve implant, which includes a hollow sphere filler, according to one embodiment.
Figure 14B:
FIG. 14B is a view of the hollow sphere filler of FIG. 14A.
Figure 14C:
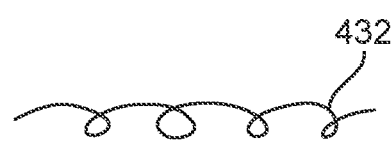
FIG. 14C is a view of the hollow sphere of FIGS. 14A and 14B stretched out.
Figure 14D:
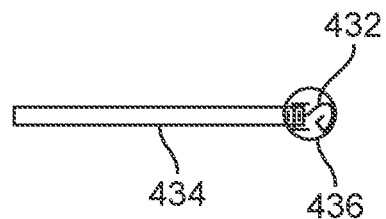
FIG. 14D is a side view of a catheter delivering the stretched out hollow sphere into the shell of the ball of FIG. 14A.

Referring now to FIGS. 14A-14D, in another embodiment, a collapsible/expandable ball 430 may include an outer shell 436 and a spiral cut elastic hollow sphere filler 432 that fills the inner cavity of the shell 436. As illustrated in FIG. 14C, the hollow sphere is made of a stretchable tube, which can be stretched for delivery through a delivery catheter (FIG. 14D) and then resumes its default spherical shape inside the shell 436 of the ball 430. The hollow sphere 432 may be formed of a superelastic material, such as Nitinol alloy, cut to form a continuous strand. As an alternative, Nitinol wire may be formed into a spherical shape, heat treated and quenched in fluid to place it into an austenitic, superelastic phase. The stretched out wire may be advanced via a catheter into the shell, expanding the shell 436 and reforming into a sphere inside the shell 436. Due to the higher forces exerted on the inside of the shell 436 as the superelastic strand or wire is advanced forward, the connection of the catheter to the self-sealing valve inside the shell 436 can be a positive mechanical joint, rather than a simple friction fit. The distal end of the catheter 434 may be externally threaded, and mate with internal threads on the inside of the self-sealing valve.

Figure 15:
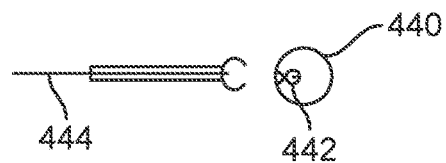
FIG. 15 is multiple views of a ball of a vascular prosthetic valve implant configured as a stretchable shell with a spring ball retainer, according to one embodiment.

Referring now to FIG. 15, in one embodiment, a balloon 440 that is fluid filled, gel filled, or air filled may be placed in a stretched configuration for delivery, to decrease its diameter to fit within a delivery catheter. The stretched balloon 440 may be released following venous insertion. A system to provide a releasable stretched balloon 440 may include an elastic balloon that contains an inner self-sealing valve. A spring ball retainer 442 is attached to the inner aspect of the self-sealing valve. The spring ball retainer 442 may be a sphere constructed of spring material such as stainless spring steel or a high durometer polymeric material such as polycarbonate or Ultem. The sphere 442 is centrally slotted along the majority of its length, and it contains a through hole in the center of its posterior aspect. The spring ball 442 retainer resides in a normally closed position. When a wire stylet 444 is inserted through the posterior hole in the spring ball retainer 442, the ball pivots open to present an enlarged vertical profile. A catheter designed to deliver and release a stretched balloon 440 contains a distal claw and an inner lumen that accommodates a wire stylet 444. The opening in the distal claw of the balloon release catheter is sized such that the balloon 440 containing a closed spring ball retainer 442 slides into the inside of the claw. However, when the wire stylet 444 is advanced through the self-sealing valve and the spring ball retainer 442, the ball retainer 442 opens in a clamshell fashion to lock the balloon 440 inside the distal claw. The wire stylet 444 is advanced further to stretch the balloon 440 axially, thereby decreasing its profile diameter.

In order to release the stretched balloon 440, the wire stylet 444 is pulled out of the spring ball retainer 442 and the self-sealing valve, causing the spring ball retainer 442 to close and the balloon 440 to exit the distal claw in the balloon release catheter. The releasable stretched balloon concept may be combined with the curable fluid filled balloon concept, but substituting the wire stylet 444 with a single or double lumen tubular stylet containing one or both of a fluid injection lumen and a curing agent lumen (e.g., a light carrying fiber optic cable). The balloon 440 may be inflated with curable fluid, the tubular stylet may be withdrawn from the spring ball retainer but not the self-sealing valve to release the balloon 440 from the distal claw, and light may be transmitted into the balloon to cure the fluid adhesive inside the balloon 440. Removal of the tubular stylet out of the self-sealing valve releases the expanded balloon 440.

Figure 16A:
FIGS. 16A and 16B are side views, illustrating a system and method for delivering a vascular prosthetic valve implant, according to one embodiment.
Figure 16B:
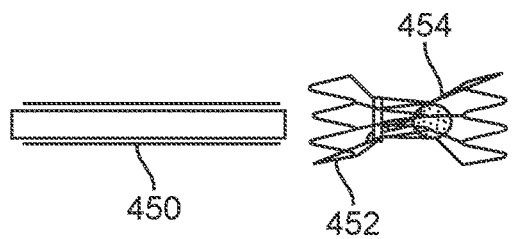

Referring now to FIGS. 16A and 16B, in some embodiments of a vascular prosthetic valve, a ball 454 may be connected to the self-expanding valve anchoring frame 452 via an elastic tether (not visible, because inside of the frame 452). One end of the elastic tether is attached to the valve frame near or at the location of the valve seat, and the other end of the tether is attached to the ball 454. As in FIG. 16A, for delivery, the elastic tether is stretched to position the ball 454 outside of the distal end of the valve frame 452. The valve frame 452 is loaded into the delivery catheter 450 in a compressed configuration, with the tethered ball 454 positioned immediately distal to the valve frame 452 in the tip of the delivery catheter 450. Upon ejection of the implant from the delivery catheter 450, as in FIG. 16B, the valve frame 452 expands, and the elastic tether contracts to pull the ball 454 into the valve frame 452. This design allows the maximal diameter of ball 454 to be accommodated inside a delivery catheter 450.

Figure 17A:
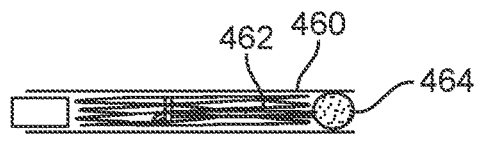
FIGS. 17A and 17B are side views, illustrating a system and method for delivering a vascular prosthetic valve implant, according to an alternative embodiment.
Figure 17B:

With reference to FIGS. 17A and 17B, in some embodiments, a ball 464 may be tethered via an inelastic tether 466 that is of sufficient length to allow the ball 464 to reside distal to the self-expanding frame 462 when the frame 462 is compressed inside the delivery catheter 460. In this design, the ball 464 has a long excursion between its closed position, in contact with the valve seat, and its open position, where it extends past the distal end of the expanded valve frame 462. This embodiment and the previously described embodiment allow for a smaller delivery catheter by moving the ball outside of the anchoring frame during loading and delivery.

Figure 18:
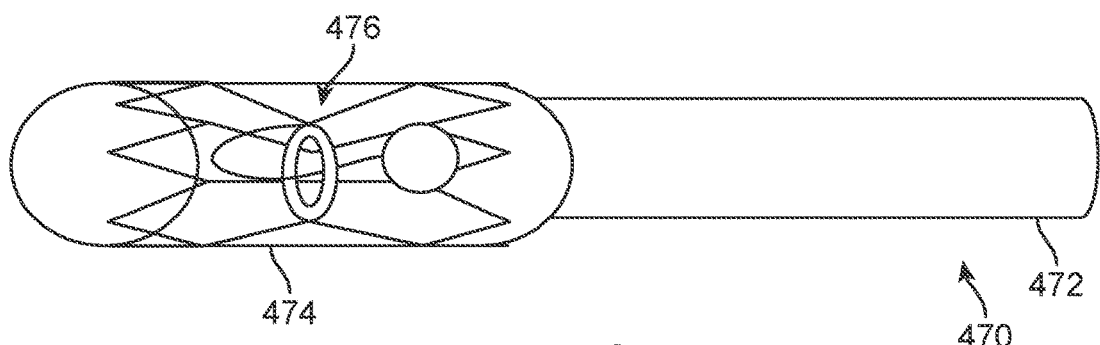
FIG. 18 is a side view, illustrating a system and method for delivering a vascular prosthetic valve implant, according to another alternative embodiment.

Referring to FIG. 18, in one embodiment, a vascular prosthetic valve delivery device 470 may include two portions—a small diameter catheter portion 472 and a larger diameter catheter portion 474. The larger diameter portion 474 may be sized to accommodate the prosthetic valve implant 476, while smaller diameter portion 472 is designed for easier advancement and maneuverability through the blood vessel. This embodiment may be combined with other approaches described in this application.

Figure 19A:
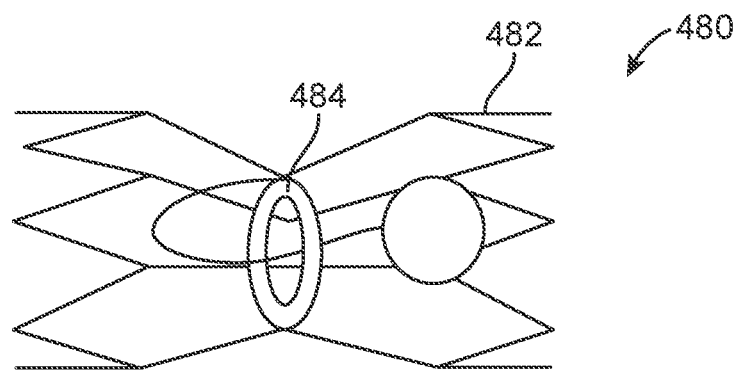
FIGS. 19A and 19B are side views of two embodiments of a vascular valve prosthetic implant having an internal ring valve seat (FIG. 19A) and an external ring valve seat (FIG. 19B), according to two alternative embodiments.

Referring now to FIG. 19A, in one embodiment of a vascular valve prosthesis 480, the valve seat may include a semi-rigid ring 484 made from material such as FEP, PTFE, or the like, attached to the anchoring frame 482. The ring 484 is configured to resist deformation post-implantation of the device 480. In this embodiment, the ring 484 is attached to an inner surface of the anchoring frame 482.

In alternative embodiments, the valve seat may be formed as part of the anchoring frame or as part of a material used to cover or coat the anchoring frame. In these embodiments, therefore, the valve seat is not a separate piece attached to the anchoring frame. For example, the valve seat in some embodiments might be a thickened portion of the anchoring frame. Alternatively, a coating substance, such as PTFE, might be used to form the valve seat. The ring embodiments of FIGS. 19A and 19B are thus merely examples.

Figure 19B:
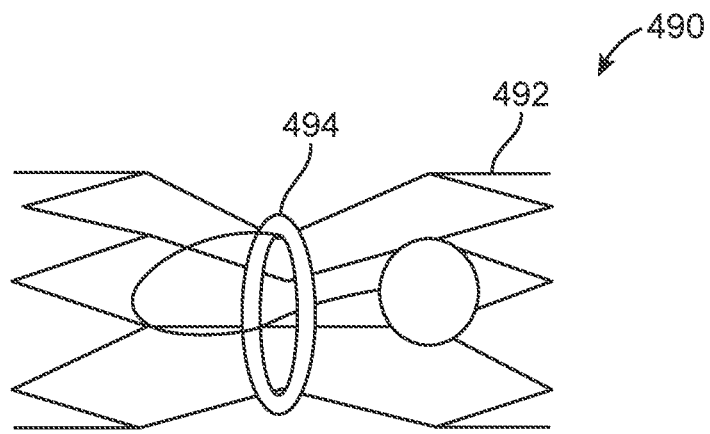

In the embodiment of FIG. 19B, the valve prosthesis 490 includes a ring 494 attached to an external surface of the anchoring frame 492. In this embodiment, the ring 494 acts as part of the anchoring member 492. In either embodiment, the ring 484, 494 may be covered or coated in the same continuous layer of material (such as PTFE) as the rest of the anchoring frame 482, 492 to allow a smooth continuous surface exposed to the blood.

In either of the two embodiments just described, as well as in any other alternative embodiments, the valve seat 484, 494 and anchoring frame 482, 492 may be sized, along with the ball, to optimize blood flow through the valve. For example, to evaluate or explain blood flow through the prosthetic valve, two different areas may be compared—the area of the opening of the valve seat and the area around the ball, between the ball and the inner wall of the anchoring member when the valve is in the open position (a flat donut shape around the ball). In some embodiments, these two areas may be designed to be exactly or approximately the same, and this may provide an advantageous flow through the valve. In other embodiments, the two areas might be within 50 percent of each other, or more ideally within 25 percent of each other, or even more ideally within 10 percent of each other.

Figure 20:
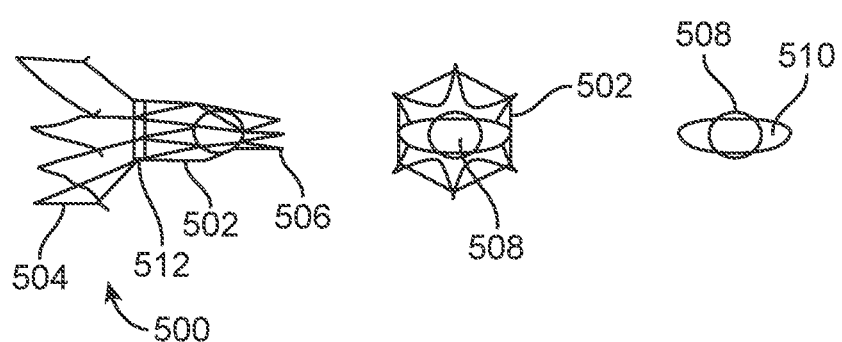
FIG. 20 is several views of a vascular prosthetic valve implant with an asymmetric expandable anchoring frame, according to one embodiment.

Referring now to FIG. 20, in another alternative embodiment, a vascular valve prosthetic implant 500 may include an asymmetric anchoring frame 502 with a valve seat 512, and a ball 508 disposed in the anchoring frame 502. The anchoring frame 502 has an asymmetrical shape, with a downstream end 506 that has a small diameter and an upstream end 504 that has a large diameter. The small downstream end 506 is small enough to constrain the ball 508, so that the ball 508 cannot escape the anchoring frame 502 from that end 506. Thus, this small diameter end 506 acts as a ball retention member or feature, so that no additional ball retention members are needed. The large diameter end 504 is large enough to anchor the anchoring frame 502 in the vein. As seen in front view in the two right hand panels, this configuration includes an elliptical valve exit orifice with two side channels 510 for blood flow around the ball 508, through the implant 500. In an alternative embodiment, the downstream end 506 could include a wide, larger diameter portion after the narrowed, small diameter portion, to prevent flow between the device and vessel wall. This would allow the same flow area at the necked down portion, while allowing device symmetry and stability at the inflow and outflow regions. Similarly, and also optionally, the small diameter end 506 may also include a large diameter anchoring portion (not shown) around the smaller, inner portion, such that both ends 504, 506 anchor in the blood vessel, even though a portion of the small diameter end 506 is still configured to trap the ball 508.

Figure 21:
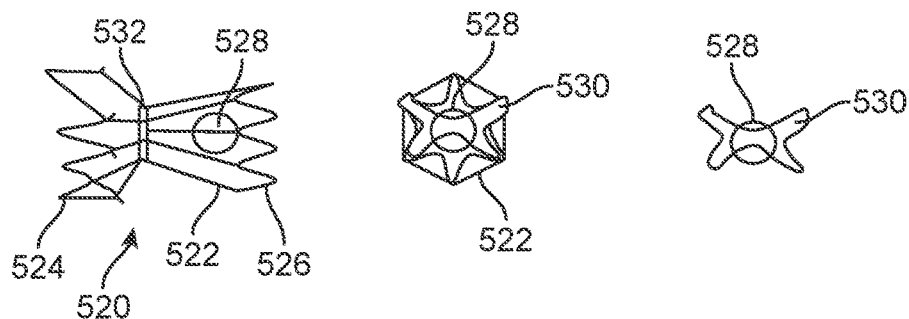
FIG. 21 is several views of a vascular prosthetic valve implant with an asymmetric expandable anchoring frame, according to an alternative embodiment.

Referring now to FIG. 21, another embodiment of a vascular valve prosthesis 520 is illustrated. The anchoring frame 522 is again asymmetric, with a wider end 524 and a narrower end 526. Also included are a ball 528 and a valve seat 532. As seen in the front views of the right hand two panels, this embodiment includes an X-shaped opening 530, which may provide for more assured constriction of the ball 528. The constricted, upstream end 526 of the superelastic frame 502 contains the ball 508 within at all times, even upon compression of the frame 502 from different directions. Following implantation, compression of the patient's thigh may occur due to applied external forces. Therefore, in this embodiment, the opening 530 includes multiple indentations to prevent the opening 530 from becoming deformed in a way that would allow the ball 528 to escape. Compression of this exit orifice 530 from any direction will collapse the crossed exit orifice 530 inwards, thereby preventing release of the ball 528. The blood flow area between the outer surface of the ball and the outline of the crossed exit orifice 530 may be greater than that of a symmetrical design. Again, the small diameter end 526 may optionally include a large diameter anchoring portion (not shown) around the smaller, inner portion, such that both ends 524, 526 anchor in the blood vessel.

Figure 22:
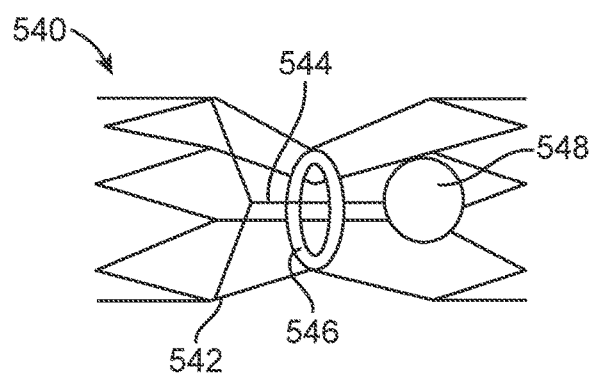
FIG. 22 is a side view of a vascular prosthetic valve implant with a V-shaped tether, according to one embodiment.

With reference now to FIG. 22, in one embodiment, a vascular valve prosthetic implant 540 may include an anchoring frame, a tether 544, a valve seat 546 and a collapsible ball 548. In previously described embodiments, ball tethers were shown as being attached at one end to the ball and at an opposite end to the valve seat or anchoring member. In this embodiment, by contrast, the tether 544 is attached at one end to the ball 548 and has an opposite end that is V-shaped and attaches to two places on the anchoring frame 542. Alternatively, the V-shaped end may split into three, four or any other number of ends that attach to the anchoring frame 542. The V-shaped, two-point attachment of the tether 544 allows the ball 548 to be placed at maximal points of shear—i.e., in the center of the valve implant 540 and may also enhance strength of the tether connection.

Figure 23:
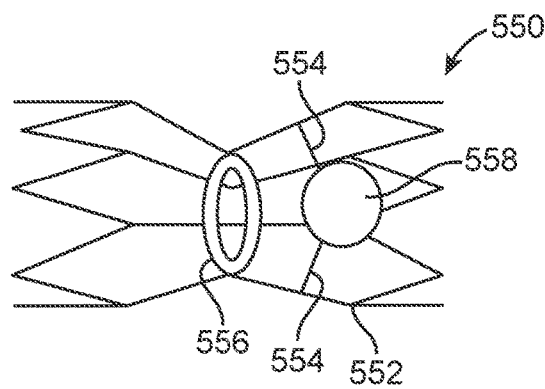
FIG. 23 is a side view of a vascular prosthetic valve implant with a two-piece tether, according to an alternative embodiment.

FIG. 23 illustrates another embodiment of a vascular valve prosthetic implant 550, including an anchoring frame 552, two tethers 554, a valve seat 556 and a collapsible ball 558. In this embodiment, the two tethers 554 are attached between the ball 548 and the anchoring frame 552. Alternatively, three, four or any other number of tethers 554 may be used.

Figure 24:
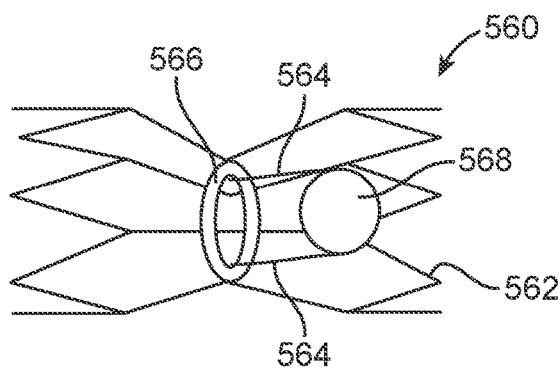
FIG. 24 is a side view of a vascular prosthetic valve implant with a two-piece tether, according to another alternative embodiment.

FIG. 24 illustrates another embodiment of a vascular valve prosthetic implant 560, including an anchoring frame 562, two tethers 564, a valve seat 566 and a collapsible ball 568. In this embodiment, the two tethers 564 are attached between the ball 568 and the anchoring frame 562. Alternatively, three, four or any other number of tethers 564 may be used. In alternative embodiments, any suitable number, length and configuration of tethers may be used.

Figure 25:
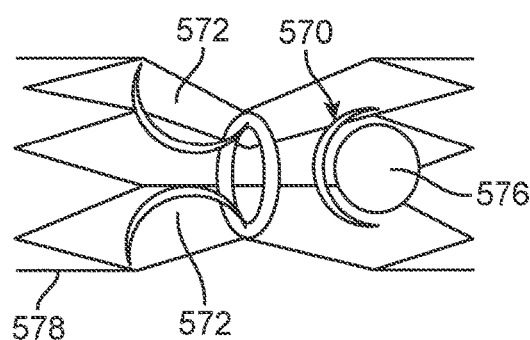
FIG. 25 is a side view of a vascular prosthetic valve implant illustrating areas of shear stress within the implant.

Referring now to FIG. 25, in some embodiments, such as those just described, the attachment locations of the tether to the anchor frame 578 and the ball 576 may be selected at least in part to try to limit clot formation at the attachment points by positioning the attachment points at locations of maximal shear (with blood flow). For example, the tether (not shown in this illustration, since these principles may be applied to many different embodiments) may be attached to the ball 576 along an area of maximal shear 570 of blood flowing around the ball 576. The tethers may also be attached to the anchoring frame 578 anywhere around the circumference of the inlet 572 that lead up to the valve seat or to the valve seat itself. These areas for locating the attachment points may help decrease the risk for thrombosis (clot formation), since they represent the areas of lowest risk for blood stagnation.

When the tether is attached to the stent valve anchor, it may be threaded through the wall of the device and tied around the outer portion of the device. It may also be fused directly to the wall of the device or valve seat of the device. Additional materials may be used or fused to cover any exit points from the device. When the tether is attached to the ball, it may be tunneled through the ball and knotted on the other end to hold it in place. It may also be tunneled and molded directly to the ball itself. It may also be one continuous piece of material. The process of attachment to the device and to the ball is important, since any disruption or irregularity in material may act as a nidus for clot formation.

Figure 26:
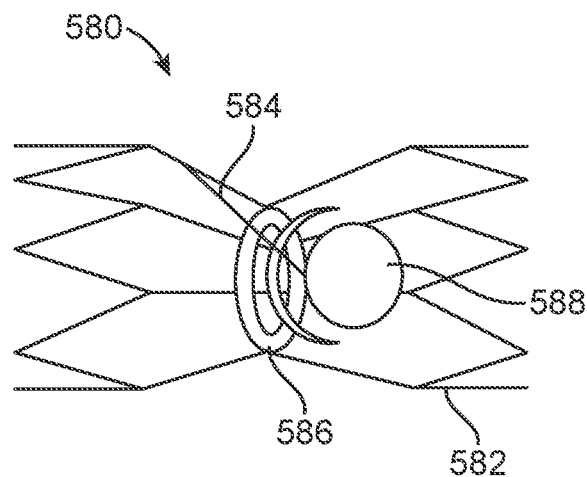
FIG. 26 is a side view of a vascular prosthetic valve implant with a short tether, according to one embodiment.

Referring now to FIG. 26, another embodiment of a vascular prosthetic valve implant 580 includes an anchoring frame 582, a tether 584, a valve seat 586 and a compressible ball 588. In this embodiment, the tether 584 is attaching to the inlet portion of the anchoring frame 582. The length of the tether 584 can be important, as it controls the location of the ball 588, which can impact clot formation. In this embodiment, the tether 584 is relatively short, so that when the valve is open, the ball 588 is located just in front of the valve seat. This may optimize flow around the ball 588, increase shear to decrease clot formation, and help hold the ball 588 in the center of the lumen of the implant 580. In various alternative embodiments, the tether 584 may have a length ranging from about 0.1 millimeters to about 25 millimeters, or more ideally between about 0.5 millimeters and about 10 millimeters.

Figure 27:
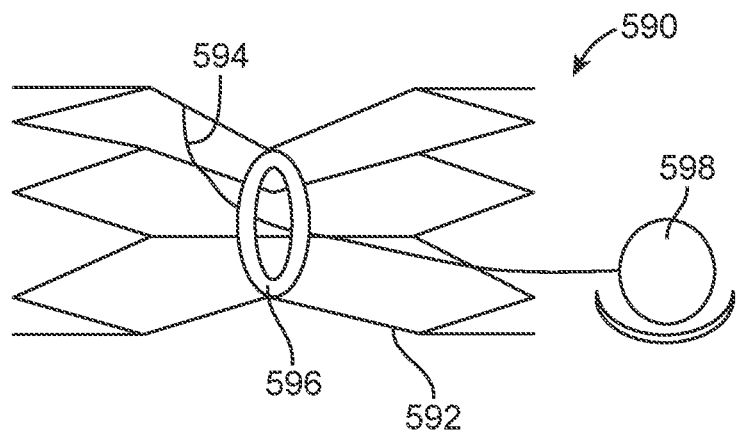
FIG. 27 is a side view of a vascular prosthetic valve implant with a long tether, according to one embodiment.

Referring to FIG. 27, an alternative embodiment of a vascular prosthetic valve implant 590 includes an anchoring frame 592, a tether 594, a valve seat 596 and a compressible ball 598. In this embodiment, the tether 594 is longer and extends beyond the end of the implant 590, such that the ball 598 sits outside the anchoring frame 592 and rests in the native vein, thus preventing foreign material from resting on foreign material. The venous wall is known to have anti-thrombotic properties, and these may prevent thrombus formation at the area of ball-wall contact.

Figure 28:
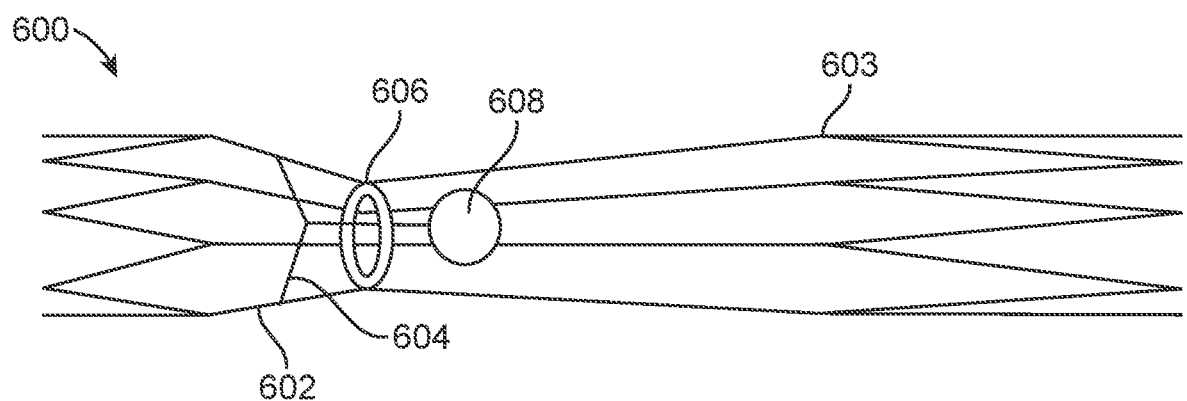
FIG. 28 is a side view of a vascular prosthetic valve implant with a long ended expandable anchoring frame, according to one embodiment.

Referring to FIG. 28, in the venous system, there is a balance between minimizing the amount of material in the blood and separating the valve portion of the device from the edge, where there is the potential for edge stenosis. The embodiment of a vascular valve prosthesis 600 in FIG. 28 includes an asymmetrical design, where the anchoring frame 602 includes a long end 603. This allows the edge that is at risk for stenosis that can lead to valve complications to be further separated from the valve itself. Depending on the vessel being treated, the long end 603 may either be proximal or distal. Also depicted in FIG. 28 are a tether 604, valve seat 606 and ball 608.

Figure 29:
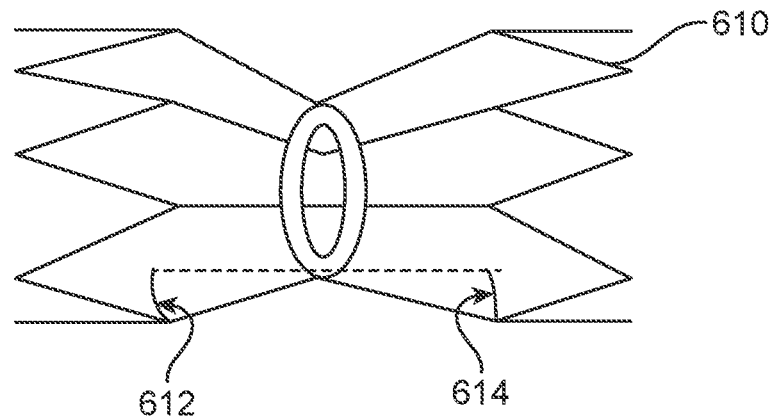
FIG. 29 is a side view of a vascular prosthetic valve implant illustrating outlet angles within the implant.

Referring to FIG. 29, an anchoring frame 610 for any of the valve prosthesis embodiments described herein may have an inlet taper angle 612 and/or an outlet taper angle 614 designed to optimize flow through the implant and prevent clot formation. In various embodiments, the angles 612, 614 may be the same or different. In general, a more gradual taper is preferred. For example, the anchoring frame 610 may have an inlet taper angle 612 and outlet taper angle 614 in the range of between about 5 degrees and about 60 degrees, or more ideally between about 15 degrees and about 35 degrees.

Figure 30:
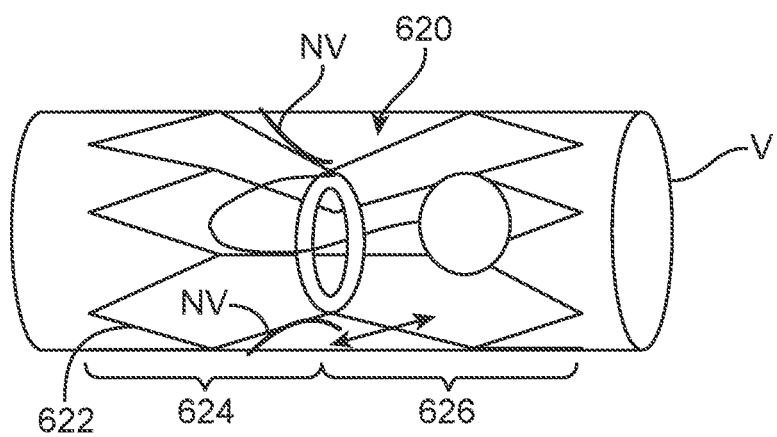
FIG. 30 is a side view of a vascular prosthetic valve implant, implanted in a vein at the location of a native venous valve, according to one embodiment.

Referring to FIG. 30, in some embodiments, a prosthetic vein valve implant 620 may have an anchoring frame 622 with a coated portion 624 and an uncoated portion 626. Additionally or alternatively, the implant 620 may be positioned within a vein V such that it lies within a native valve NV. Either or both of these features (the uncoated portion 626 and the placement in the native valve NV) may help stimulate the vein V to secrete anti-thrombotic agents. For example, if the entire portion 626 of the implant 620 after the valve seat is not coated with a hemostatic layer, blood will accumulate in the space between the implant 620 and the wall of the vein V. The vein's antithrombotic agents can decrease likelihood of clot in that area, similar to the natural vein valve NV. Similarly, if the implant 620 is placed such that the native valve NV lies on the implant 620, it can further decrease risk of clotting via native anti-coagulant. This also creates a more physiologic space similar to the native leaflet valve NV.

FIGS. 31A-31C depict yet another alternative embodiment of a venous valve prosthesis 630, in this case it includes an anchoring frame 632, a ball retention member 636, a flap valve 634 with an opening 635 that acts as the valve seat, and a ball 638. FIG. 31A is a partial cross-sectional view, depicting the ball 638 seated in the opening 635 of the flap valve 634 (front view in FIG. 31B), such that the implant 630 is in its closed position. In FIG. 31C, the valve implant 630 is in the open position, with the flap valve 634 oriented in the opposite direction and the ball 638 located between the flap valve 634 and the ball retention member 636. The flap valve 634 may be made of a thin material that can invert and evert, as illustrated in FIGS. 31A and 31C. Blood flows through the opening 635 in one direction, but when blood flows in the other direction the ball 638 seals the hole 635 and prevents retrograde flow. In an alternative embodiment, a tether may be used instead of the ball retention member 636.

Referring now to FIG. 32, in some embodiments, an anchoring frame 640 for a vascular valve prosthesis may include multiple anti-migration barbs 642 that are located apart from either of the two extreme ends of the frame 640. Anti-migration features (such as barbs 642) were explained above and are generally configured to prevent the anchoring frame 640 from moving within the vein or other blood vessel after it has been delivered. As opposed to some of the embodiments described above, the barbs 642 of this embodiment of the anchoring frame 640 are positioned away from the two extreme ends of the anchoring frame 640. Barbs 642 in this location help anchor the valve implant and prevent device migration and may also be less prone to the fibrotic reaction that may be promoted by barbs positioned at the proximal and distal edges of an anchoring frame. The barbs 642 are not in an area at high risk for stenosis and are not exposed to the flow of blood, due to the continuous layer of PTFE over the anchoring frame. This is important in decreasing the risk of edge stenosis and potential failure of the device. In alternative embodiments, the barbs 642 may be positioned only towards one end of the anchoring frame 640, rather than near both ends as depicted in FIG. 32.

Figure 33:
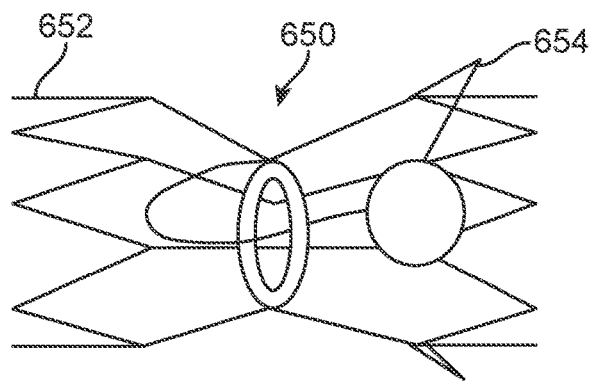
FIG. 33 is a side view of an expandable anchoring frame of a vascular prosthetic valve implant, having V-shaped protrusions protruding outward in locations separate from the ends of the frame, according to one embodiment.

With reference now to FIG. 33, in another embodiment, a venous valve implant 650 may include an anchoring frame 652 with multiple anti-migration V-shaped protrusions 654, rather than single-point barbs. The V-shaped protrusions 654 may also be located away from either of the extreme ends of the anchoring frame 652, and they may help maintain the valve implant 650 in the blood vessel and prevent it from migrating. Alternative embodiments may include U-shaped protrusions, hooks or any other configuration of anti-migration members. And again, the V-shaped protrusions 654 may be located near either end of the anchoring frame 652 in some embodiments and need not be near both ends.

In various embodiments, the anti-migration barbs 642, V-shaped protrusions 654 or other anti-migration features may form any of a range of angles, relative to the adjacent portion of the anchoring frame 640, 650 from which they protrude. For example, in some embodiments, the anti-migration features may form an angle with the anchoring frame 640, 650 of between about 15 degrees and about 60 degrees, or more ideally between about 25 degrees and about 45 degrees.

Figure 34A:
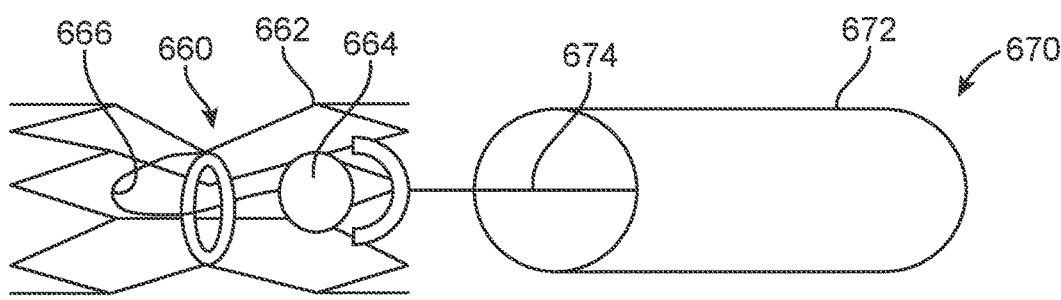
FIGS. 34A-34C are side view of an a system and method for removing a ball from an implanted vascular prosthetic valve implant, according to one embodiment.
Figure 34B:
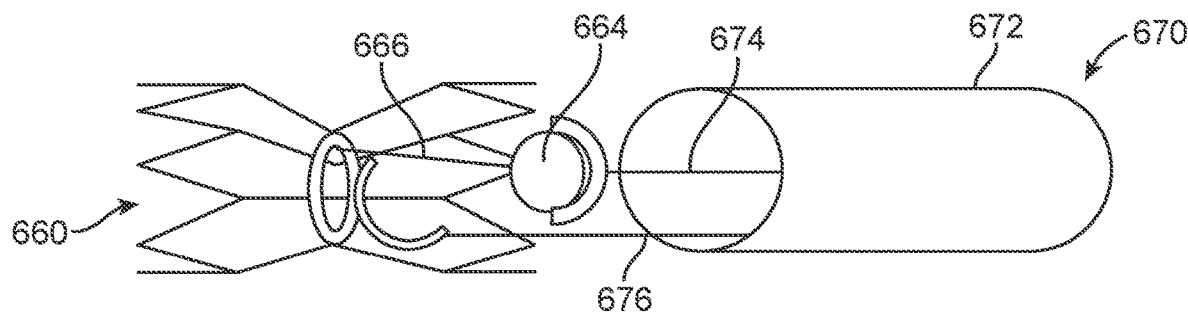
Figure 34C:
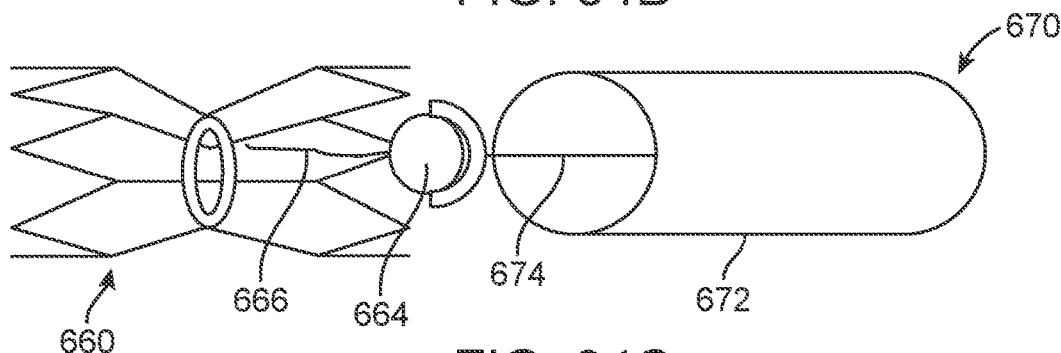

Referring to FIGS. 34A-34C, in some embodiments, it may be desirable to remove the ball from a vascular valve implant, for example to replace it with a new ball. As illustrated in FIG. 34A, a vascular valve implant 660 includes an expandable anchoring frame 662, a ball 664 and a tether 666, as described above in relation to many embodiments. A ball removal device 670 may be advanced into the vein to remove the ball 664. The ball removal device 670 includes a catheter 672, a grasper 674 and a tether cutter 676. In FIG. 34A, the grasper 674 is advanced out of the catheter 672 toward the ball 664. In FIG. 34B, the grasper 674 has been used to grasp the ball 664, and the tether cutter 676 is advanced to cut the tether 666. In FIG. 34C, the cutter 676 has cut the tether 666 and has been retracted back into the catheter 672. The grasper 674 may then be used to pull the ball 664 out of the valve implant 660. The grasper 674 may attach to the ball 664 via suction, magnetic attraction, adhesion, or any other suitable mechanical attachment or modality. The ball 664 may then be pulled toward the catheter 672 to draw the tether 666 taught before using the cutter 676. The cutter 676 may have a scissors end or any other suitable cutting device end. After the ball 664 is removed, the anchoring frame 662 may remain in place in the vessel. The ball 664 may be replaced by a new ball, in some embodiments.

In alternative embodiments, the valve implant may not include a tether, and the tether cutter 676 may not be needed. Thus, a ball removal device, in an alternative embodiment, may include only the catheter 672 and the grasper 674.

Figure 35A:
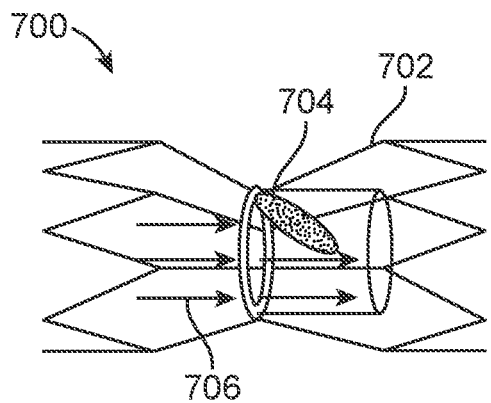
FIGS. 35A and 35B are side views of a vascular prosthetic valve implant with a single leaf flap valve, according to one embodiment.
Figure 35B:
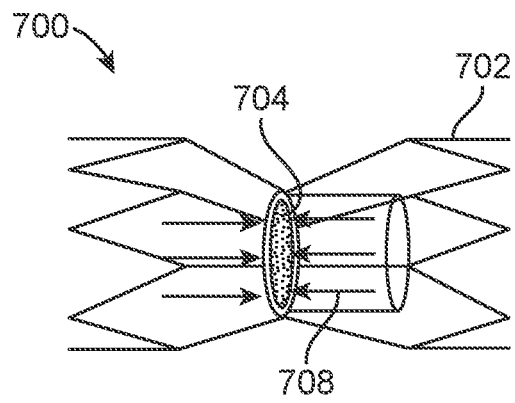

Referring to FIGS. 35A and 35B, in one alternative embodiment, a venous valve implant 700 may include an expandable anchoring frame 702 and a single leaflet flap valve 704. FIG. 35A shows the valve 704 in the open position allowing blood 706 to flow though the implant 700. FIG. 35B shows the valve 704 in the closed position, preventing retrograde blood flow 708 through the implant 700.

Figure 36A:
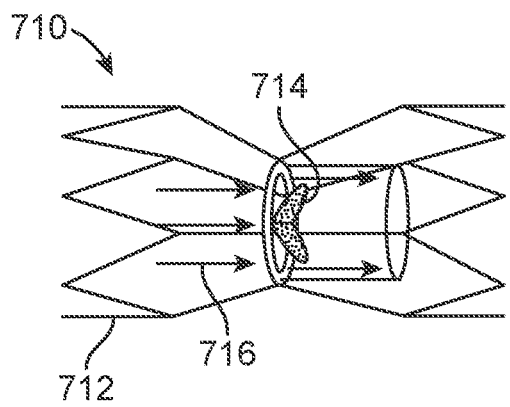
FIGS. 36A and 36B are side views of a vascular prosthetic valve implant with a single leaf flap valve, according to one embodiment.
Figure 36B:
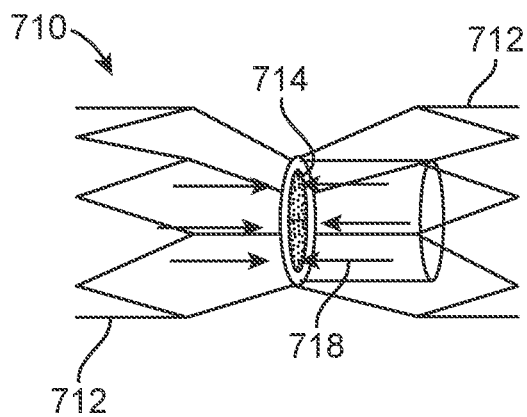

In another alternative embodiment, shown in FIGS. 36A and 36B, a venous valve implant 710 may include an expandable anchoring frame 712 and a two leaflet flap valve 714. FIG. 36A shows the valve 714 in the open position allowing blood 716 to flow though the implant 710. FIG. 36B shows the valve 714 in the closed position, preventing retrograde blood flow 718 through the implant 710. In either of the two leaflet valve embodiments 700, 710, the flap(s) of the valve 704, 714 may be made of delrin, titanium, silastic, Teflon, silicone coated Teflon, pyrolyte, or any other suitable leaflet material. The valves 704, 714 are mechanical valves and are thus different than prior leaflet valves, which are bioprosthetic, thin, and more prone to failure. Further, placement in the expandable/collapsible anchoring frame 702, 712 allows for easier delivery in a percutaneous system.

Figure 37A:
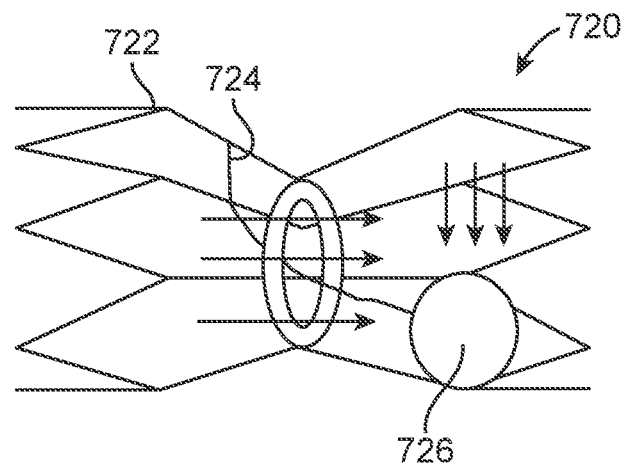
FIGS. 37A and 37B are side views of a vascular prosthetic valve implant with a tether, illustrating the effects of gravity on the ball of the implant.
Figure 37B:
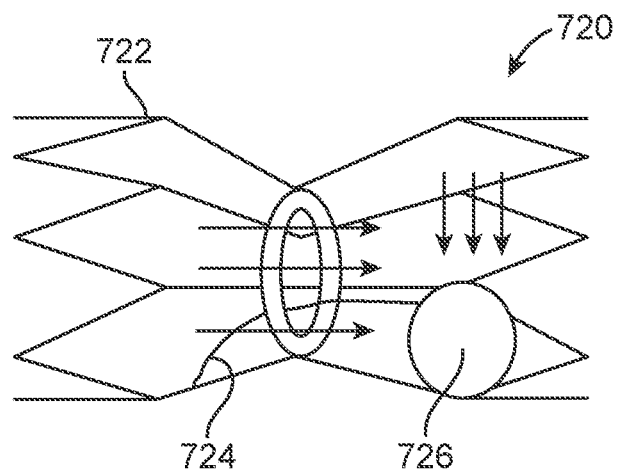

FIGS. 37A and 37B illustrate the effect of gravity on one embodiment of a venous valve prosthetic implant 720, which includes an expandable anchoring frame 722, a tether 724 and a ball 726. In certain non-symmetric embodiments, such as one leveraging a single tether 724, orientation of the implant 720 can alter how the ball 726 moves and rests in the vascular system. For example, if the patient is in a sitting or supine position, gravity will push the ball 726 downward, and the flow of blood will push the ball sideways, as depicted in FIGS. 37A and 37B. The tether attachment location, relative to the direction of the gravitational force, can impact the likelihood that the ball gets "kicked up" by the blood flow and moves within the implant 720. FIG. 37A depicts the forces and a tether orientation that will enhance ball movement. The tether orientation depicted in FIG. 37B is less likely to enhance ball movement. Increased ball movement leads to fewer areas of stasis or minimized blood flow, and therefore decreases likelihood of clot. Therefore, orientation of the venous valve implant 720 can play an important role in the success of the implant 720. In this or other embodiments, one or more radiopaque markers may be placed on the implant 720 and/or on the delivery catheter to visualize orientation of the implant 720 on fluoroscopy during implantation. The delivery catheter can be rotated in order to orient the valve implant 720 appropriately prior to deployment from the catheter. This allows control of orientation upon deployment. Alternatively, the delivery catheter handle can have a demarcation or indicator that corresponds to the orientation of the valve implant 720 in the sheath. This catheter can then be appropriately rotated in order to orient the valve prior to deployment.

Figure 38:
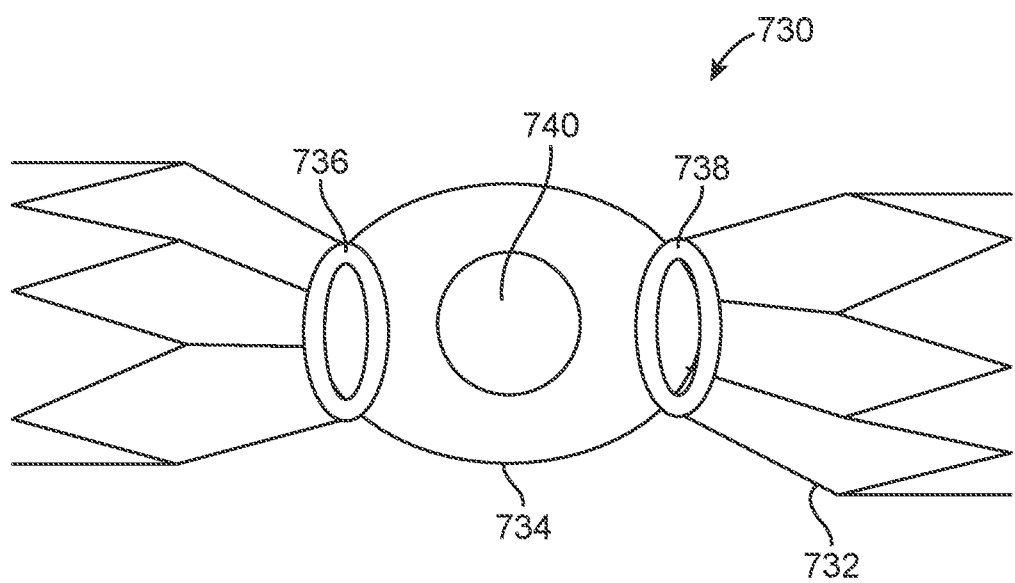
FIG. 38 is a side view of a vascular prosthetic valve implant with an anchoring member with a central round portion, according to one embodiment.

FIG. 38 depicts an alternate embodiment of a venous valve implant 730, which includes an expandable anchoring frame 732 with two end portions and a central round portion 734, a valve seat 736, a ball retention member 738 and a ball 740. The central round portion 734 of the anchoring frame 732 may provide for more uniform forward blood flow around the ball 740, with decreased areas of stasis due to sudden changes in geometry or angles. As the geometry of the anchoring frame 732 encourages blood flow back behind the ball 740, this helps prevent an area of stasis that would otherwise be seen behind the ball 740. More uniform blood flow and decreased areas of stasis help prevent thrombus formation and device failure. In alternative embodiments, the central round portion 734 may be more elongate, more oval-shaped or the like. In other alternative embodiments, a tether may be used to retain the ball 740.

Previously disclosed ball-valve type venous valve prostheses include a self-expanding anchor frame and a polymer ball with a density greater than the density of blood, to ensure that the ball would move into contact with the valve seat and close properly when the patient is in either an upright or a supine position. In one embodiment, for example, the density of the polymer ball may be approximately 2.2 g/cm3, while the density of blood is approximately 1.06 g/cm3. In alternative embodiments, it may be advantageous to use a ball that has a lower density than 2.2 g/cm3. Some embodiments of the venous valve implant, for example, may use polymer balls of a density nearly or approximately equal to the density of blood (1.06 g/cm3). Such a ball is referred to as a "neutral density ball" in this disclosure. Active movement of the neutral density ball may help prevent thrombus formation on the ball. In various embodiments, the neutral density ball of a venous ball valve prosthesis may have a density of less than about 2.2 g/cm3. More preferably, the ball may have a density between about 0.9 g/cm3 and about 1.2 g/cm3. In one embodiment, the ball may have a density of about 1.06 g/cm3. The neutral density of the ball may be achieved in any of several suitable ways. First, a material that has a natural density within that range (e.g., polyurethane) may be used. Alternatively, a material with a natural density lower than that range may be weighted to have an effective density within the range.

As discussed above, it is also desirable for the ball of the venous valve implant to be compressible, as this allows the implant to be introduced via a smaller diameter catheter. The compressible ball may be made of a biocompatible flexible foam, such as polyurethane or silicone rubber. A foam ball that exhibits a significant degree of compressibility is also characterized by a low density. For example, a 7 mm diameter polyurethane foam ball that may be compressed to fit into a catheter with a 4 mm inner diameter may have a density of 0.064 g/cc, compared to the density of blood at 1.06 g/ml. Thus, the foam is approximately 1/16th the density of blood, and weight must be added to the foam ball to render it functional as a valve.

Figure 39A:
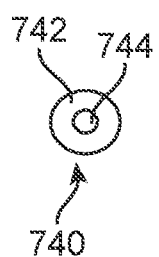
FIGS. 39A and 39B are side views of a ball without and with a tether, respectively, of a vascular prosthetic valve implant, according to one embodiment.
Figure 39B:
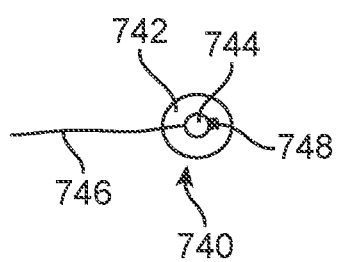

Referring now to FIGS. 39A and 39B, in one embodiment, a ball 740 of a venous valve implant may include a compressible foam outer portion 742 and a weighted core 744, which may be a spherical stainless steel ball, for example. As depicted in FIG. 39B, the compressible foam outer portion 742 and the core 744 may both have an aperture, through which a tether 746 may pass. (The aperture is not visible in the drawing.) The aperture may pass all the way through the core 744, so that the tether 746 may be knotted 748 outside of one end of the aperture. The tether 746 may be any suitable tether material, as described above, such as a monofilament formed of polytetrafluoroethylene (PTFE).

Figure 40:
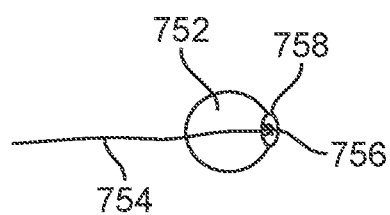
FIG. 40 is a side view of a ball and a tether of a vascular prosthetic valve implant, according to an alternative embodiment.

Referring now to FIG. 40, in an alternative embodiment of a venous valve implant, a foam ball 752 (or other lightweight ball material) may be used without a weight but instead with an elastic tether 754. The compressible foam ball 752 resides on one side of the valve seat, and the elastic tether 754 is attached to the valve frame (not illustrated) on the opposite side of the valve seat. The elastic tether 754 is attached to the frame under tension, so the compressible foam ball is biased against the valve seat with a calibrated force. The calibrated force may be equivalent to a ball of identical outer diameter containing a density close to the density of blood. The elastic tether 754 may extend through the diameter of the compressible foam ball 752. The distal end of the elastic tether 754 may be knotted, and the knot 756 may be retracted into a cutaway in the foam ball 752. The knot 756 may be covered with implantable grade adhesive filler 758 to yield a smooth contour to the surface of the foam ball 752 at the site of the knot 756. The elastic tether 754 may be constructed of silicone rubber, polyurethane, or other elastic material. It may be a solid strand containing a round cross-section, with an outer diameter of approximately 0.1-0.2 mm.

Figure 41:
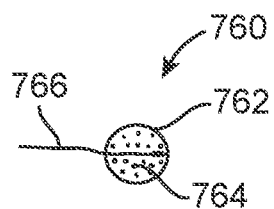
FIG. 41 is a side view of a ball and a tether of a vascular prosthetic valve implant, according to another alternative embodiment.

Referring to FIG. 41, in another embodiment, a compressible ball 760 for a vascular valve implant may include a compressible ball portion 762 with multiple higher density weights 764, such as stainless steel microspheres, dispersed throughout the ball portion 762. This allows the ball 760 to have the same overall desired density, while allowing more complete compressibility. The ball 760 may also include an aperture extending through its diameter to accommodate a tether 766, as described above.

As mentioned previously, a venous valve prosthesis with a tethered ball having a density nearly neutral to blood and also being compressible and self-expanding is advantageous, as it allows the prosthesis to be delivered via a delivery catheter with a significantly smaller outer diameter than is possible with a rigid, non-compressible ball. A compressible ball may be constructed of flexible polyurethane foam, as polyurethane foam is biocompatible and relatively non-thrombogenic. Flexible polyurethane foam is available that may be molded from two-part liquid mixtures that are combined and subsequently self-expand to form a compressible solid. Some of these foams form an outer skin that renders them fluid-tight.

In order to form flexible foam that is characterized by high compressibility; e.g. 10:1 compressibility, the resultant solid foam typically needs to have a density much lower than blood (e.g. 0.064 g/cm3 compared to the density of blood at 1.06 g/cm3). Weight may be added to such a compressible foam ball, to render it density-neutral to blood. Biocompatible weights 764, such as stainless-steel microspheres, may be added to the mold during the formation of the foam ball 760. For example, microspheres of 0.5 mm to 1.0 mm may be distributed within the flexible foam ball portion 762, providing a ball density neutral to blood while still allowing it to be compressed substantially within the valve frame for insertion via a small diameter delivery catheter. The stainless-steel microspheres 764 incorporated in the polyurethane foam ball portion 762 render the ball 760 radiopaque for visibility during fluoroscopic examination. Alternatively, barium sulfate powder may be mixed into the polyurethane foam, to provide sufficient weight to form a blood neutral density foam ball 760 that is also radiopaque.

The inelastic tether that attaches the foam ball to the valve frame may be composed of PTFE monofilament suture, for example. Attachment of the tether to the foam ball may be performed in several ways. In one embodiment, a knot is tied near the end of the PTFE suture, the knotted suture is pulled into a central channel formed in the foam ball, and ultraviolet curable adhesive is used to glue the suture inside the channel. In another embodiment, a short length of thick-walled stainless-steel tubing is crimped near the distal end of the suture, and the crimped suture is glued into the central channel in the foam ball. Alternatively, the foam may be molded around the suture or a knotted end of the suture. In other alternative embodiments, the suture may be attached to one of the microspheres with foam subsequently being molded over it.

Alternatively, mechanical means can be used to hold the ball in the central lumen of the device to avoid ball to wall device contact. For example, a semi-rigid tether (e.g., Nitinol) can be used to allow the ball to translate proximally and distally in the body and device, but not medially or laterally to rest on the wall of the device. This allows the ball to still act as a functional valve, while avoiding ball to wall contact.

Figure 42A:
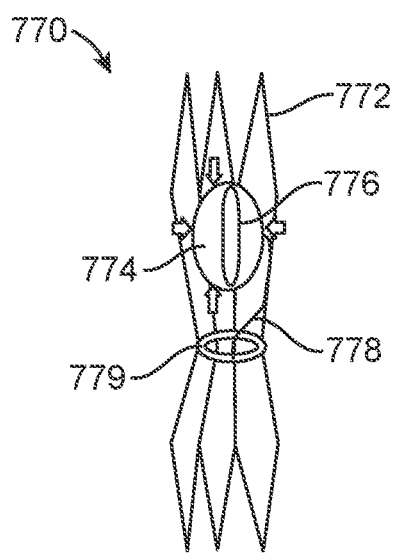
FIGS. 42A and 42B are side views of a vascular prosthetic valve implant with a ball having a central rod, according to one embodiment.
Figure 42B:
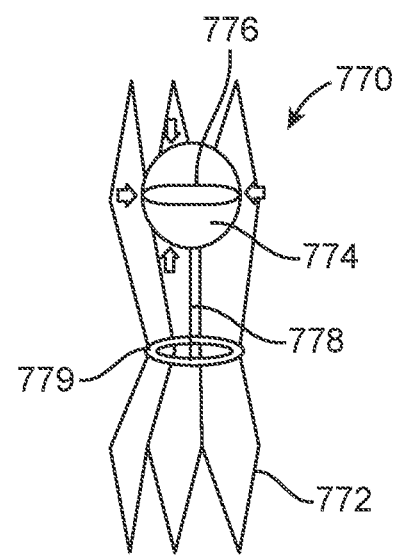

Referring to FIGS. 42A and 42B, in some embodiments, compressibility of a vascular valve implant 770 may be limited or focused in certain dimensions. For example, in the depicted embodiment, the implant 770 includes an expandable anchoring frame 772, a collapsible ball 774, a tether 778 and a valve seat 779, among other features. The ball 774 includes a central rod 776, which may be made of metal, plastic or other rigid material. As illustrated in FIG. 42A, when the rod 776 is oriented longitudinally, the ball 774 and the anchoring frame 772 may be collapsed, such as for delivery through a delivery catheter. As illustrated in FIG. 42B, when the rod 776 is oriented horizontally (or perpendicular to the longitudinal axis of the anchoring frame 772), the rod 776 prevents the ball from collapsing inwards toward the center of the frame 772. In other words, the rod 776 allows the ball 774 to compress in two dimensions, but not three. In some embodiments, the tether 778 may be attached to the rod 776. By orienting the tether 778 perpendicular to the central rod/restrictor 776, when the device 770 is deployed (FIG. 42B), the ball 774 will be prevented from squeezing through, or wedging into, the valve seat 779. This design allows the ball 774 to be of lower density and compressible, while also preventing the ball 774 from being compressed and squeezed through the valve seat 779 due to backpressure.

The invention claimed is:

1. A venous valve prosthetic implant for treating a vein, the implant comprising:
   a tubular, expandable anchoring frame, consisting of a stent extending from an upstream end to a downstream end of the implant, wherein the anchoring frame forms a lumen from the upstream end to the downstream end, and wherein the anchoring frame comprises;
      a cylindrical upstream portion at the upstream end;
      a cylindrical downstream portion at the downstream end;
      an inwardly angled inlet portion between the cylindrical upstream portion and a middle of the anchoring frame; and
      an inwardly angled outlet portion between the cylindrical downstream portion and the middle of the anchoring frame;
   a valve seat formed at or near the middle of the anchoring frame;
   an expandable ball disposed within the lumen of the anchoring frame, between the valve seat and the downstream end, wherein the expandable ball expands from a compressed configuration for delivery into the vein through a delivery catheter to an expanded configuration outside the delivery catheter, and wherein the expandable ball in the expanded configuration moves between an open position, in which the expandable ball is located apart from the valve seat, to allow forward flow of blood through the implant, and a closed position, in which the expandable ball contacts the valve seat to prevent backflow of blood through the implant, wherein the expandable ball has a density of less than 2.5 grams per square centimeter; and
   a ball retention tether having a first end attached to the expandable ball and a second end attached to at least one of the valve seat or the anchoring frame at a location that is upstream of a downstream end of the ball at least when the ball is in a most downstream position.

2. The implant of claim 1, further comprising a material disposed over at least part of the anchoring frame.

3. The implant of claim 2, wherein the material is made of at least one substance selected from the group consisting of polymers, hyaluronic acid, heparin and anticoagulant agents.

4. The implant of claim 1, wherein the anchoring frame comprises multiple outward facing protrusions on at least one of the upstream portion, apart from the upstream end, or the downstream portion, apart from the downstream end.

5. The implant of claim 4, wherein the multiple outward facing protrusions are selected from the group consisting of barbs, hooks, U-shaped protrusions and V-shaped protrusions.

6. The implant of claim 1, wherein the valve seat comprises a ring attached to at least one of an inner surface or an outer surface of the anchoring member.

7. The implant of claim 1, wherein the expandable ball comprises a solid, compressible foam ball.

8. The implant of claim 1, wherein the expandable ball comprises:
   an elastic shell; and
   a filler substance inside the elastic shell.

9. The implant of claim 8, wherein the filler substance is selected from the group consisting of air, gels, a solid weight and fluids.

10. The implant of claim 8, wherein the filler substance comprises a curable substance that hardens when cured.

11. The implant of claim 8, wherein the filler substance comprises a spiral-cut, elastic, hollow sphere.

12. The implant of claim 1, wherein the expandable ball comprises an aperture through which the ball retention tether is passed.

13. The implant of claim 1, wherein the expandable ball has a density of no greater than 1.06 grams per square centimeter, and wherein the tether is elastic, to pull the ball toward the valve seat to prevent backflow of blood through the implant.

14. The implant of claim 1, wherein the inlet portion and the outlet portion of the anchoring frame each form an angle, relative to a longitudinal axis of the implant, of between 15 degrees and 35 degrees.

15. The implant of claim 1, wherein the ball retention tether has a length of between 0.5 millimeters and 10 millimeters.

16. The implant of claim 1, wherein the expandable ball is made of a material selected from the group consisting of thermoplastic polyurethane, elastomeric thermoplastic polyurethane, PVC, Polyethylene, polycarbonate, PEEK, ultem, PEI, polypropylene, polysulfone, FEP, PTFE, coated hollow heavy metal and combinations thereof.

17. A venous valve prosthetic implant system for treating a vein, the system comprising:
  an implant, comprising:
    a tubular, expandable anchoring frame, consisting of a stent extending from an upstream end to a downstream end of the implant, wherein the anchoring frame forms a lumen from the upstream end to the downstream end, and wherein the anchoring frame comprises;
      a cylindrical upstream portion at the upstream end;
      a cylindrical downstream portion at the downstream end;
      an inwardly angled inlet portion between the cylindrical upstream portion and a middle of the anchoring frame; and
      an inwardly angled outlet portion between the cylindrical downstream portion and the middle of the anchoring frame;
    a valve seat formed at or near the middle of the anchoring frame;
    an expandable ball disposed within the lumen of the anchoring frame, between the valve seat and the downstream end, wherein the expandable ball expands from a compressed configuration for delivery into the vein through a delivery catheter to an expanded configuration outside the delivery catheter, and wherein the expandable ball in the expanded configuration moves between an open position, in which the expandable ball is located apart from the valve seat, to allow forward flow of blood through the implant, wherein the expandable ball has a density of less than 2.5 grams per square centimeter, and a closed position, in which the expandable ball contacts the valve seat to prevent backflow of blood through the implant; and
    a ball retention tether having a first end attached to the expandable ball and a second end attached to at least one of the valve seat or the anchoring frame at a location that is upstream of a downstream end of the ball at least when the ball is in a most downstream position; and
  a delivery device, comprising:
    an elongate, flexible catheter body; and
    a deployment plunger disposed within the catheter body for pushing the implant out of the catheter body.

18. The system of claim 17, wherein the deployment plunger comprises a curing member for curing a curable material of which the expandable ball is at least partially made.

19. The system of claim 18, wherein the curing member is configured to emit a curing agent selected from the group consisting of heat, light, electricity, sound waves, and a chemical mixture.

20. The system of claim 17, wherein the delivery device further comprises an inflation tube disposed within the catheter body, wherein the inflation tube comprises a distal end configured to enter an aperture in the expandable ball to inflate the expandable ball.

21. The system of claim 20, wherein the inflation tube further comprises a curing member configured to emit a curing agent selected from the group consisting of heat, light, electricity, sound waves, and a chemical mixture.

22. The system of claim 17, wherein the delivery device further comprises an inflation attachment configured for passing fluid through a lumen in at least one of the valve seat or the ball retention tether to inflate the expandable ball.

23. The system of claim 17, further comprising a ball extraction device configured to extract the expandable ball from the implant.

24. The system of claim 23, wherein the ball extraction device comprises:
  a grasper for grasping the expandable ball; and
  a cutter for cutting a tether attaching the expandable ball to at least one of the anchoring frame or the valve seat.

25. The system of claim 23, wherein the ball extraction device is configured to pass through the catheter body of the delivery device.

26. The system of claim 17, wherein the delivery device further includes at least one orientation indicator for indicating an orientation of the implant within the catheter body.

* * * * *

UNITED STATES PATENT AND TRADEMARK OFFICE
CERTIFICATE OF CORRECTION

PATENT NO. : 10,912,647 B2  
APPLICATION NO. : 16/007471  
DATED : February 9, 2021  
INVENTOR(S) : Albert K Chin et al.

Page 1 of 1

It is certified that error appears in the above-identified patent and that said Letters Patent is hereby corrected as shown below:

On the Title Page

On the page 2, in item (60), in Column 1, in "Related U.S. Application Data", Line 2, delete "2016," and insert -- 2015, --, therefor.

In the Specification

In Column 3, Line 59, delete "centimeter." and insert -- centimeter, --, therefor.
In Column 7, Line 5, delete "an a" and insert -- a --, therefor.
In Column 10, Line 27, delete "teraphthalate)," and insert -- terephthalate), --, therefor.
In Column 24, Line 58, delete "pyrolyte," and insert -- pyrolite, --, therefor.

In the Claims

In Column 30, Lines 4-8, in Claim 17, delete "the implant, wherein the expandable ball has a density of less than 2.5 grams per square centimeter, and a closed position, in which the expandable ball contacts the valve seat to prevent backflow of blood through the implant; and" and insert -- the implant, and a closed position, in which the expandable ball contacts the valve seat to prevent backflow of blood through the implant, wherein the expandable ball has a density of less than 2.5 grams per square centimeter; and --, therefor.

Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*